US008311891B2

(12) United States Patent
Berkelhamer et al.

(10) Patent No.: US 8,311,891 B2
(45) Date of Patent: Nov. 13, 2012

(54) SYSTEM FOR SEPARATING AND DISTRIBUTING PHARMACY ORDER PROCESSING FOR MEDICATION PAYMENTS

(75) Inventors: Alan J. Berkelhamer, Highland Park, IL (US); Gowri Selka, Buffalo Grove, IL (US)

(73) Assignee: Walgreen Co., Deerfield, IL (US)

( * ) Notice: Subject to any disclaimer, the term of this patent is extended or adjusted under 35 U.S.C. 154(b) by 1269 days.

(21) Appl. No.: 11/252,759

(22) Filed: Oct. 18, 2005

(65) Prior Publication Data

US 2007/0088565 A1    Apr. 19, 2007

(51) Int. Cl.
*G06F 19/00* (2006.01)
*G06Q 10/00* (2006.01)
(52) U.S. Cl. .................... 705/20; 705/2; 705/3
(58) Field of Classification Search .............. 705/2, 3, 705/4
See application file for complete search history.

(56) References Cited

U.S. PATENT DOCUMENTS

| | | |
|---|---|---|
| 4,457,772 A | 7/1984 | Haynes et al. |
| 4,852,001 A | 7/1989 | Tsushima et al. |
| 5,053,970 A | 10/1991 | Kurihara et al. |
| 5,072,383 A | 12/1991 | Brimm et al. |
| 5,260,868 A | 11/1993 | Gupta et al. |
| 5,289,370 A | 2/1994 | Lirov |
| 5,337,919 A | 8/1994 | Spaulding et al. |
| 5,548,518 A | 8/1996 | Dietrich et al. |
| 5,559,710 A | 9/1996 | Shahraray et al. |
| 5,597,995 A | 1/1997 | Williams et al. |
| 5,615,121 A | 3/1997 | Babayev et al. |
| 5,619,991 A | 4/1997 | Sloane |
| 5,630,070 A | 5/1997 | Dietrich et al. |
| 5,737,539 A | 4/1998 | Edelson et al. |
| 5,737,728 A | 4/1998 | Sisley et al. |
| 5,748,907 A | 5/1998 | Crane |
| 5,758,095 A | 5/1998 | Albaum et al. |
| 5,765,139 A | 6/1998 | Bondy |
| 5,771,657 A | 6/1998 | Lasher et al. |
| 5,790,785 A | 8/1998 | Klug et al. |
| 5,797,515 A | 8/1998 | Liff et al. |
| 5,801,755 A | 9/1998 | Echerer |
| 5,826,236 A | 10/1998 | Narimatsu et al. |
| 5,826,252 A | 10/1998 | Wolters, Jr. et al. |
| 5,845,255 A | 12/1998 | Mayaud |
| 5,852,259 A | 12/1998 | Yanase et al. |
| 5,907,493 A | 5/1999 | Boyer et al. |

(Continued)

FOREIGN PATENT DOCUMENTS

EP         0921 488 A1    6/1999
(Continued)

OTHER PUBLICATIONS

Anonymous, "CVS, Merck-Medco in E-commerce Alliance," Chain Drug Review, 21(18):2 (1999).

(Continued)

*Primary Examiner* — Robert Morgan
*Assistant Examiner* — Sean K Hunter
(74) *Attorney, Agent, or Firm* — Francis C. Kowalik; Marshall, Gerstein & Borun LLP; Randall G. Rueth

(57) ABSTRACT

An information system and method that provides the ability to reroute portions of prescription order work between a plurality of organizational units in order to leverage capacity, expertise, or other resources to increase network efficiency.

19 Claims, 15 Drawing Sheets

U.S. PATENT DOCUMENTS

| | | |
|---|---|---|
| 5,911,687 A | 6/1999 | Sato et al. |
| 5,915,240 A | 6/1999 | Karpf |
| 5,924,074 A | 7/1999 | Evans |
| 5,946,883 A | 9/1999 | Yuyama et al. |
| 5,954,640 A | 9/1999 | Szabo |
| 5,963,911 A | 10/1999 | Walker et al. |
| 5,970,462 A | 10/1999 | Reichert |
| 5,987,519 A | 11/1999 | Peifer et al. |
| 6,067,524 A | 5/2000 | Byerly et al. |
| 6,078,912 A | 6/2000 | Buerger et al. |
| 6,112,182 A | 8/2000 | Akers et al. |
| 6,202,080 B1 | 3/2001 | Lu et al. |
| 6,202,923 B1 | 3/2001 | Boyer et al. |
| 6,208,973 B1 * | 3/2001 | Boyer et al. ............... 705/2 |
| 6,256,550 B1 | 7/2001 | Wu et al. |
| 6,266,655 B1 | 7/2001 | Kalyan |
| 6,294,999 B1 | 9/2001 | Yarin et al. |
| 6,311,163 B1 | 10/2001 | Sheehan et al. |
| 6,317,719 B1 | 11/2001 | Schrier et al. |
| 6,330,491 B1 | 12/2001 | Lion |
| 6,347,329 B1 | 2/2002 | Evans |
| 6,364,517 B1 | 4/2002 | Yuyama et al. |
| 6,370,841 B1 | 4/2002 | Chudy et al. |
| 6,381,577 B1 | 4/2002 | Brown |
| 6,397,190 B1 | 5/2002 | Goetz |
| 6,421,650 B1 | 7/2002 | Goetz et al. |
| 6,438,451 B1 | 8/2002 | Lion |
| 6,463,417 B1 | 10/2002 | Schoenberg |
| 6,464,142 B1 | 10/2002 | Denenberg et al. |
| 6,477,442 B1 | 11/2002 | Valerino, Sr. |
| 6,493,427 B1 | 12/2002 | Kobylevsky et al. |
| 6,496,427 B2 | 12/2002 | Kojima et al. |
| 6,523,009 B1 | 2/2003 | Wilkins |
| 6,539,281 B2 | 3/2003 | Wan et al. |
| 6,564,121 B1 | 5/2003 | Wallace et al. |
| 6,625,952 B1 | 9/2003 | Chudy et al. |
| 6,665,740 B1 | 12/2003 | Mason, Jr. et al. |
| 6,711,460 B1 | 3/2004 | Reese |
| 6,735,497 B2 | 5/2004 | Wallace et al. |
| 6,741,724 B1 | 5/2004 | Bruce et al. |
| 6,874,684 B1 | 4/2005 | Denenberg et al. |
| 6,947,900 B2 | 9/2005 | Giordano, III et al. |
| 7,058,584 B2 | 6/2006 | Kosinski et al. |
| 7,111,780 B2 | 9/2006 | Broussard et al. |
| 7,139,639 B2 | 11/2006 | Broussard et al. |
| 7,711,583 B2 | 5/2010 | Epstein et al. |
| 7,801,642 B2 | 9/2010 | Ansari et al. |
| 7,941,325 B2 | 5/2011 | Heald et al. |
| 7,987,107 B2 | 7/2011 | Wilson et al. |
| 2001/0009005 A1 | 7/2001 | Godin et al. |
| 2002/0019786 A1 | 2/2002 | Gonzalez et al. |
| 2002/0032583 A1 * | 3/2002 | Joao ............... 705/2 |
| 2002/0052770 A1 | 5/2002 | Podrazhansky |
| 2002/0062175 A1 | 5/2002 | Lion |
| 2002/0062230 A1 | 5/2002 | Morag et al. |
| 2002/0120573 A1 | 8/2002 | McCormick |
| 2002/0153411 A1 | 10/2002 | Wan et al. |
| 2002/0188467 A1 | 12/2002 | Eke |
| 2002/0198454 A1 | 12/2002 | Seward et al. |
| 2003/0074234 A1 | 4/2003 | Stasny |
| 2003/0109950 A1 | 6/2003 | Andrade et al. |
| 2003/0149599 A1 | 8/2003 | Goodall et al. |
| 2003/0179287 A1 | 9/2003 | Kozic et al. |
| 2003/0225595 A1 * | 12/2003 | Helmus et al. ............... 705/2 |
| 2004/0019794 A1 | 1/2004 | Moradi et al. |
| 2004/0088187 A1 | 5/2004 | Chudy et al. |
| 2004/0117046 A1 | 6/2004 | Colle et al. |
| 2004/0122713 A1 | 6/2004 | Hill et al. |
| 2004/0133705 A1 | 7/2004 | Broussard et al. |
| 2004/0172289 A1 | 9/2004 | Kozic et al. |
| 2004/0220829 A1 | 11/2004 | Baharav et al. |
| 2004/0221034 A1 | 11/2004 | Kausik et al. |
| 2004/0260577 A1 | 12/2004 | Dahlin et al. |
| 2005/0075902 A1 | 4/2005 | Wager et al. |
| 2005/0125798 A1 | 6/2005 | Peterson |
| 2005/0267356 A1 | 12/2005 | Ramasubramanian et al. |
| 2006/0041330 A1 | 2/2006 | Ansari et al. |
| 2006/0149587 A1 | 7/2006 | Hill et al. |
| 2006/0253346 A1 | 11/2006 | Gomez |
| 2006/0276933 A1 | 12/2006 | Chavez et al. |
| 2006/0287906 A1 | 12/2006 | McGillin |
| 2007/0067186 A1 | 3/2007 | Brenner et al. |
| 2007/0088565 A1 | 4/2007 | Berkelhamer et al. |
| 2007/0088566 A1 | 4/2007 | Berkelhamer et al. |
| 2007/0088567 A1 | 4/2007 | Berkelhamer et al. |
| 2007/0088568 A1 | 4/2007 | Goodall et al. |
| 2007/0088569 A1 | 4/2007 | Berkelhamer et al. |
| 2007/0088590 A1 | 4/2007 | Berkelhamer et al. |
| 2007/0088596 A1 | 4/2007 | Berkelhamer et al. |
| 2007/0168301 A1 | 7/2007 | Eisner et al. |
| 2007/0250341 A1 | 10/2007 | Howe et al. |

FOREIGN PATENT DOCUMENTS

| | | |
|---|---|---|
| JP | 361217880 A | 9/1986 |
| WO | WO-96 13790 | 5/1996 |
| WO | WO-0108393 A1 | 2/2001 |

OTHER PUBLICATIONS

Anonymous, "Name Change Reflects CVS' Commitment to E-commerce," Chain Drug Review, 21(15):2 (1999).

Walgreens On-line Prefills (Website Printout Packet—printed Jul. 5, 2006) archived as Jun. 17, 1998, p. 1-13.

Colchamiro, "Independents Look to Go Online," American Druggist, Sep. 1999, pp. 1-3.

McNaughton, "Can Net Drugstores Outpace The Chains?" CNET News.com, Feb. 24, 1999, 1 page.

Wolverton, "Online Pharmacies Partner For Power," CNET News.com, Oct. 8, 1999, pp. 1-2.

"The Virtual Pharmacist," Rural Electric, vol. 60, No. 6, Mar. 2002, p. 20.

U.S. Appl. No. 09/715,872, filed Nov. 15, 2000, entitled "Apparatus and Method for Accessing Pharmacy Information and Ordering Prescriptions."

U.S. Appl. No. 11/252,775, filed Oct. 18, 2005, entitled "Method and Apparatus for Inter-Pharmacy Workload Balancing."

U.S. Appl. No. 11/253,252, filed Oct. 18, 2005, entitled "System for Separating and Distributing Pharmacy Order Processing."

U.S. Appl. No. 11/252,947, filed Oct. 18, 2005, entitled "System for Separting and Distributing Pharmacy Order Processing for Compound Medication."

U.S. Appl. No. 11/252,776, filed Oct. 18, 2005, entitled "System for Separating and Distributing Pharmacy Order Processing for Specialty Medication."

U.S. Appl. No. 11/253,253, filed Oct. 18, 2005, entitled "System for Separating and Distributing Pharmacy Order Processing for Out of Stock Medication."

U.S. Appl. No. 11/253,185, filed Oct. 18, 2005, entitled "System for Separating and Distributing Pharmacy Order Processing for Prescription Verification."

U.S. Appl. No. 11/253,096, filed Oct. 18, 2005, entitled "Method and Apparatus for Inter-Pharmacy Workload Balancing Using Resource Function Assignments."

Final Office action for U.S. Appl. No. 11/252,947 dated Oct. 4, 2010.

Office Action for U.S. Appl. No. 12/248,774 dated Oct. 28, 2010.

Final Office Action issued U.S. Appl. No. 11/253,185 dated Jan. 8, 2010.

Office Action issued in U.S. Appl. No. 11/252,776 dated Sep. 28, 2009.

Office Action issued in U.S. Appl. No. 11/252,947 dated Sep. 2, 2009.

Office Action issued in U.S. Appl. No. 11/253,096 dated Jun. 10, 2009.

Office Action issued in U.S. Appl. No. 11/253,252 dated Sep. 3, 2009.

Office Action issued in U.S. Appl. No. 11/253,253 dated Jul. 20, 2009.

Final Office Action issued in U.S. Appl. No. 11/252,775 dated Sep. 29, 2009.

Office action for U.S. Appl. No. 11/252,947 dated Mar. 17, 2010.

Final Office action for U.S. Appl. No. 11/253,252 dated Mar. 5, 2010.

Final Office action for U.S. Appl. No. 11/252,776 dated Apr. 22, 2010.

Final Office action for U.S. Appl. No. 11/253,253 dated Mar. 9, 2010.

Office action for U.S. Appl. No. 11/252,947 dated Apr. 4, 2011.
Final Office action for U.S. Appl. No. 11/252,947 dated Sep. 15, 2011.
Office action for U.S. Appl. No. 11/252,776 filed Sep. 30, 2011.
Office action for U.S. Appl. No. 12/248,769 dated Mar. 9, 2011.
Final Office action for U.S. Appl. No. 12/248,769 dated Aug. 5, 2011.
Office action for U.S. Appl. No. 12/248,774 dated Oct. 18, 2011.
Final Office action for U.S. Appl. No. 12/248,774 dated Apr. 5, 2011.
Office action for U.S. Appl. No. 13/076,958 dated Nov. 4, 2011.
Office action for U.S. Appl. No. 12/271,686 dated Feb. 15, 2011.

Final Office action for U.S. Appl. No. 12/271,686 dated Aug. 10, 2011.
Office action for U.S. Appl. No. 12/271,069 dated Jan. 25, 2011.
Final Office action for U.S. Appl. No. 12/271,069 dated Jun. 23, 2011.
"Optimize your Enterprise for Maximum Profitability," NDCHealth, May 5, 2005, 4 pages.

* cited by examiner

SYSTEM FOR SEPARATING AND DISTRIBUTING PHARMACY ORDER PROCESSING FOR MEDICATION PAYMENTS

FIELD OF THE INVENTION

The present invention generally relates to a process for managing prescription order workflow in a pharmacy network.

BACKGROUND

Prescription drug orders have traditionally been processed by a single retail store, even when the retail store belongs to a larger network of affiliated stores. Differences in the number and types of transactions processed by resources at individual stores within a network may result in a system wide inefficiency. This is particularly true where a single retail store performs all of the processing steps for each received prescription. Currently, there is no way for a pharmacy network to benefit by more efficiently using its network resources to sub-divide work into portions that are processed by different organizational units.

SUMMARY OF THE INVENTION

The method and system enables a product work order to be divided into portions that may be distributed and processed by a plurality of organizational units within a pharmacy network.

Original order data, which may take the form of an unprocessed, scanned-in prescription image, is entered into a network computer and associated with a task object. Processed information relating to a prescription order is captured by the task object. The task object may be passed between various organizational units in order to distribute processing of tasks and functions associated with the prescription order.

Each organizational unit may contain a queue. A workflow may define a sequence of queues. To complete the distributed processing of the prescription order, the task object may be passed along the queues, where each queue corresponds to a portion of work in processing a prescription order. The original order data object may be referenced in the task object or passed along with the task object.

This system enables flexible pharmacy organization planning and allows for implementation of different workflows for different types of work orders. While the specific method and system will be described to apply to a pharmacy retail network embodiment, it is emphasized that this process may be applied to other retail network systems that require original order data to be referenced during the processing of a work order. Other network systems may include those for various technical products, legal document processing, and/or forensic processing.

DETAILED DESCRIPTION

Although the following text sets forth a detailed description of numerous different embodiments, it should be understood that the legal scope of the invention is defined by the words of the claims set forth at the end of this patent. The detailed description is to be construed as exemplary only and does not describe every possible embodiment since describing every possible embodiment would be impractical, if not impossible. Numerous alternative embodiments could be implemented, using either current technology or technology developed after the filing date of this patent, which would still fall within the scope of the claims.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph.

Figure 1:
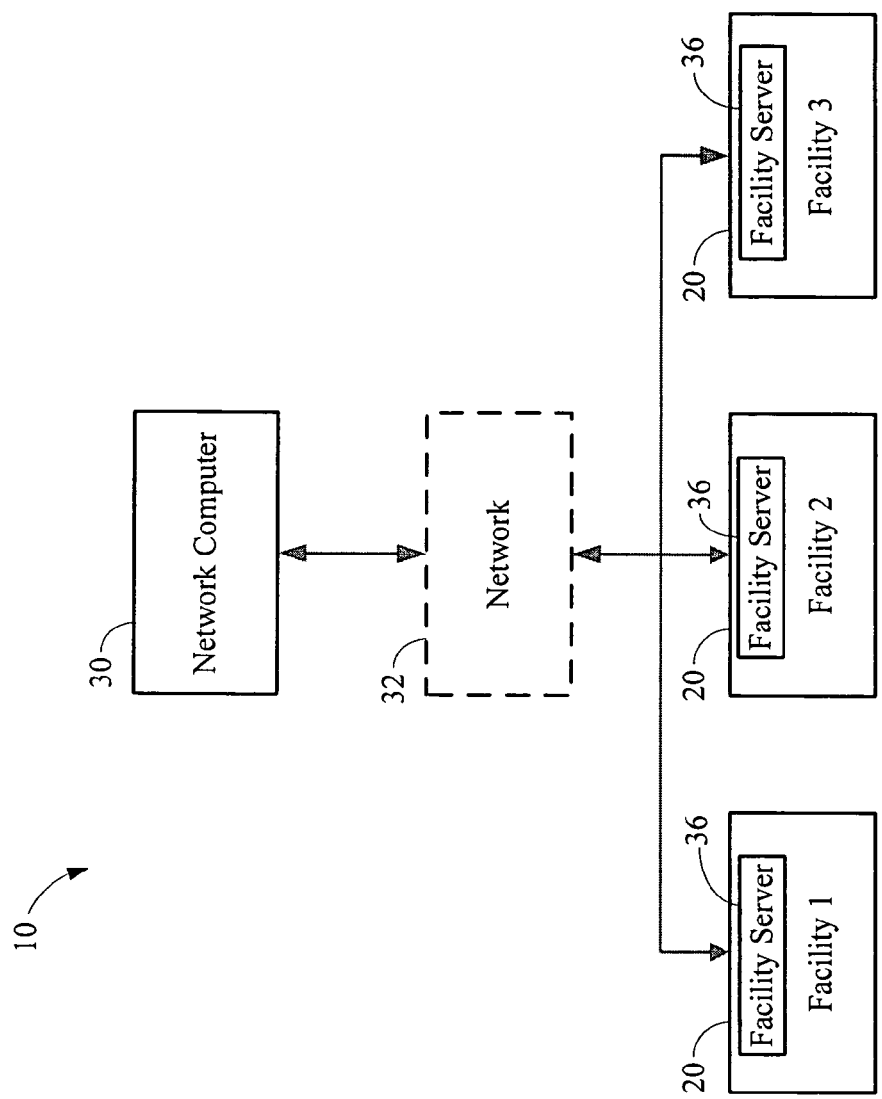
FIGS. 1-3 illustrate block diagrams of a computing system that may operate in accordance with the described embodiments.

FIG. 1 illustrates an embodiment of a data network 10 including a first group of pharmacies 20 operatively coupled to a network computer 30 via a network 32. The plurality of pharmacies 20 may be located, by way of example rather than limitation, in separate geographic locations from each other, in different areas of the same city, or in different states. The network 32 may be provided using a wide variety of techniques well known to those skilled in the art for the transfer of electronic data. For example, the network 32 may comprise dedicated access lines, plain ordinary telephone lines, satellite links, combinations of these, etc. Additionally, the network 32 may include a plurality of network computers or server computers (not shown), each of which may be operatively interconnected in a known manner. Where the network 32 comprises the Internet, data communication may take place over the network 32 via an Internet communication protocol.

The network computer 30 may be a server computer of the type commonly employed in networking solutions. The network computer 30 may be used to accumulate, analyze, and download pharmacy data. For example, the network computer 30 may periodically receive data from each of the pharmacies 20 indicative of information pertaining to a prescription order, billing information, employee data, etc. The pharmacies 20 may include one or more facility servers 36 that may be utilized to store information for a plurality of customers/employees/accounts/etc. associated with each facility.

Although the data network 10 is shown to include one network computer 30 and three pharmacies 20, it should be understood that different numbers of computers and pharmacies may be utilized. For example, the network 32 may include a plurality of network computers 30 and dozens of pharmacies 20, all of which may be interconnected via the network 32. According to the disclosed example, this configuration may provide several advantages, such as, for example, enabling near real time uploads and downloads of information as well as periodic uploads and downloads of information. This provides for a primary backup of all the information generated in the process of updating and accumulating pharmacy data.

Figure 2:
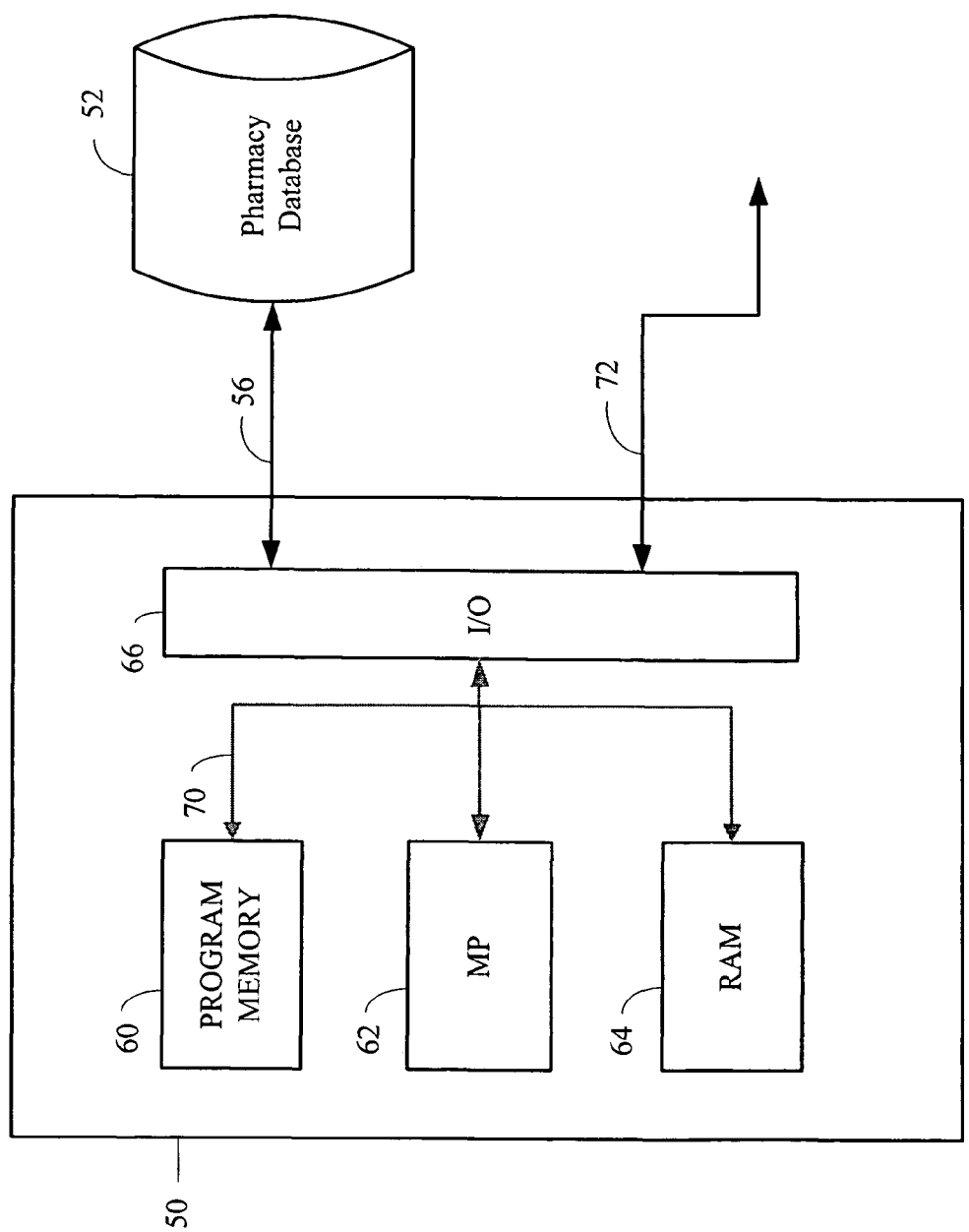

FIG. 2 is a schematic diagram of one possible embodiment of the network computer 30 shown in FIG. 1. The network computer 30 may have a controller 50 that is operatively connected to a database 52 via a link 56. It should be noted that, while not shown, additional databases may be linked to the controller 50 in a known manner.

The controller 50 may include a program memory 60, a microcontroller or a microprocessor (MP) 62, a random-access memory (RAM) 64, and an input/output (I/O) circuit 66, all of which may be interconnected via an address/data bus 70. It should be appreciated that although only one microprocessor 62 is shown, the controller 50 may include multiple microprocessors 62. Similarly, the memory of the controller 50 may include multiple RAMs 64 and multiple program memories 60. Although the I/O circuit 66 is shown as a single block, it should be appreciated that the I/O circuit 66 may include a number of different types of I/O circuits. The RAM(s) 64 and programs memories 60 may be implemented as semiconductor memories, magnetically readable memories, and/or optically readable memories, for example. The controller 50 may also be operatively connected to the network 32 via a link 72.

Figure 3:
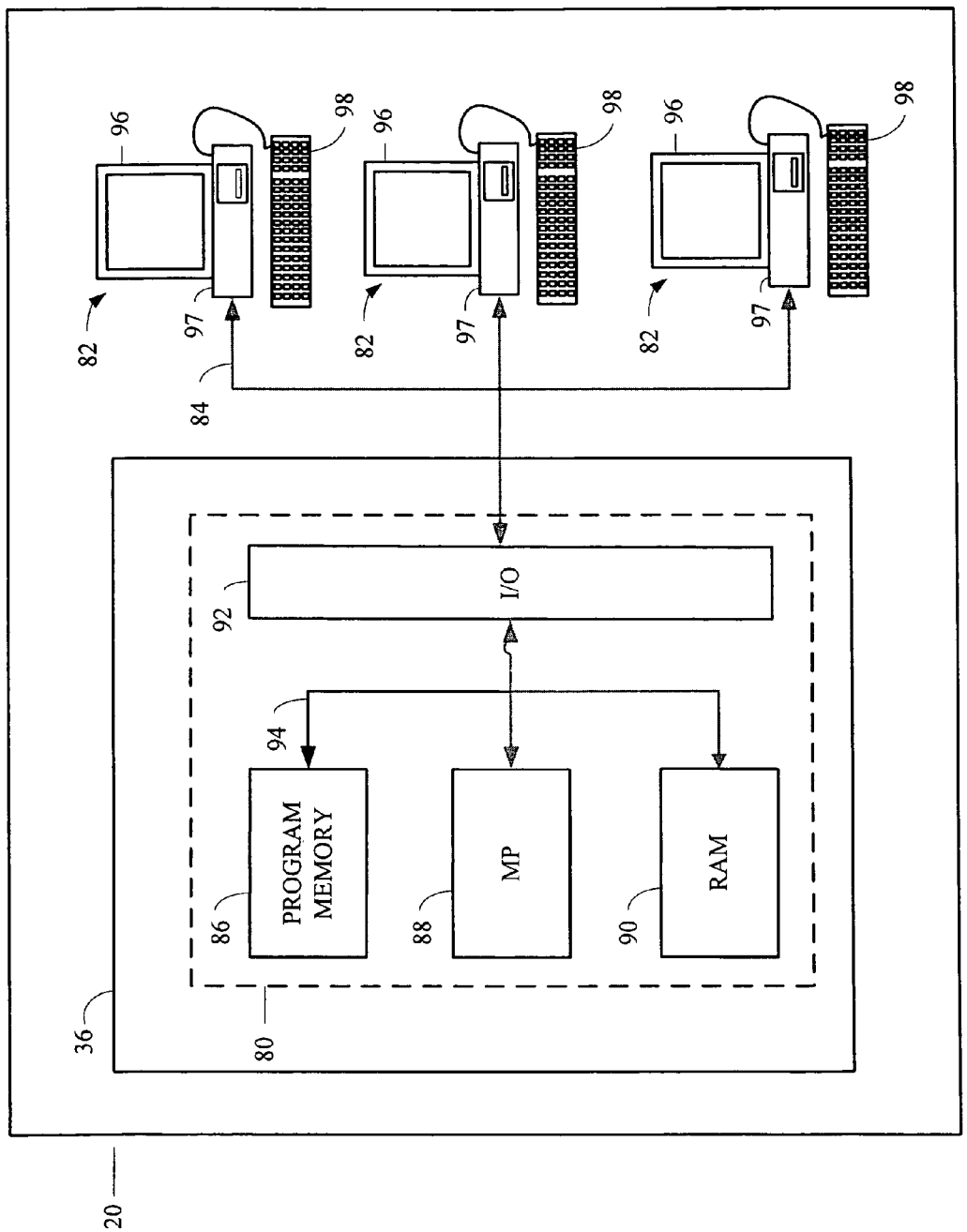

FIG. 3 is a schematic diagram of one possible embodiment of several components located in one or more of the pharmacies 20 from FIG. 1. Although the following description addresses the design of the pharmacies 20, it should be understood that the design of one or more of the pharmacies 20 may be different than the design of other pharmacies 20. Also, each pharmacy 20 may have various different structures and methods of operation. It should also be understood that the embodiment shown in FIG. 3 illustrates some of the components and data connections present in a pharmacy, however it does not illustrate all of the data connections present in a typical pharmacy. For exemplary purposes, one design of a pharmacy is described below, but it should be understood that numerous other designs may be utilized.

The pharmacies 20 may have a facility server 36, which includes a controller 80, wherein the facility server 36 is operatively connected to a plurality of client device terminals 82 via a network 84. The network 84 may be a wide area network (WAN), a local area network (LAN), or any other type of network readily known to those persons skilled in the art. The client device terminals 82 may also be operatively connected to the network computer 30 from FIG. 1 via the network 32.

Similar to the controller 50 from FIG. 2, the controller 80 may include a program memory 86, a microcontroller or a microprocessor (MP) 88, a random-access memory (RAM) 90, and an input/output (I/O) circuit 92, all of which may be interconnected via an address/data bus 94. As discussed with reference to the controller 50, it should be appreciated that although only one microprocessor 88 is shown, the controller 80 may include multiple microprocessors 88. Similarly, the memory of the controller 80 may include multiple RAMs 90 and multiple programs memories 86. Although the I/O circuit 92 is shown as a single block, the I/O circuit 92 may include a number of different types of I/O circuits. The RAM(s) 90 and programs memories 86 may also be implemented as semiconductor memories, magnetically readable memories, and/or optically readable memories, for example.

The client device terminals 82 may include a display 96, a controller 97, a keyboard 98 as well as a variety of other input/output devices (not shown) such as a scanner, printer, mouse, touch screen, track pad, track ball, isopoint, voice recognition system, etc. Each client device terminal 82 may be signed onto and occupied by a pharmacy employee to assist them in performing their duties. Pharmacy employees may sign onto a client device terminal 82 using any generically available technique, such as entering a user name and password. If a pharmacy employee is required to sign onto a client device terminal 82, this information may be passed via the link 84 to the facility server 36, so that the controller 80 will be able to identify which pharmacy employees are signed onto the system and which client device terminals 82 the employees are signed onto. This may be useful in monitoring the pharmacy employees' productivity.

Typically, facility servers 36 store a plurality of files, programs, and other data for use by the client device terminals 82 and the network computer 30. One facility server 36 may handle requests for data from a large number of client device terminals 82. Accordingly, each facility server 36 may typically comprise a high end computer with a large storage capacity, one or more fast microprocessors, and one or more high speed network connections. Conversely, relative to a typical facility server 36, each client device terminal 82 may typically include less storage capacity, a single microprocessor, and a single network connection.

Figure 4:
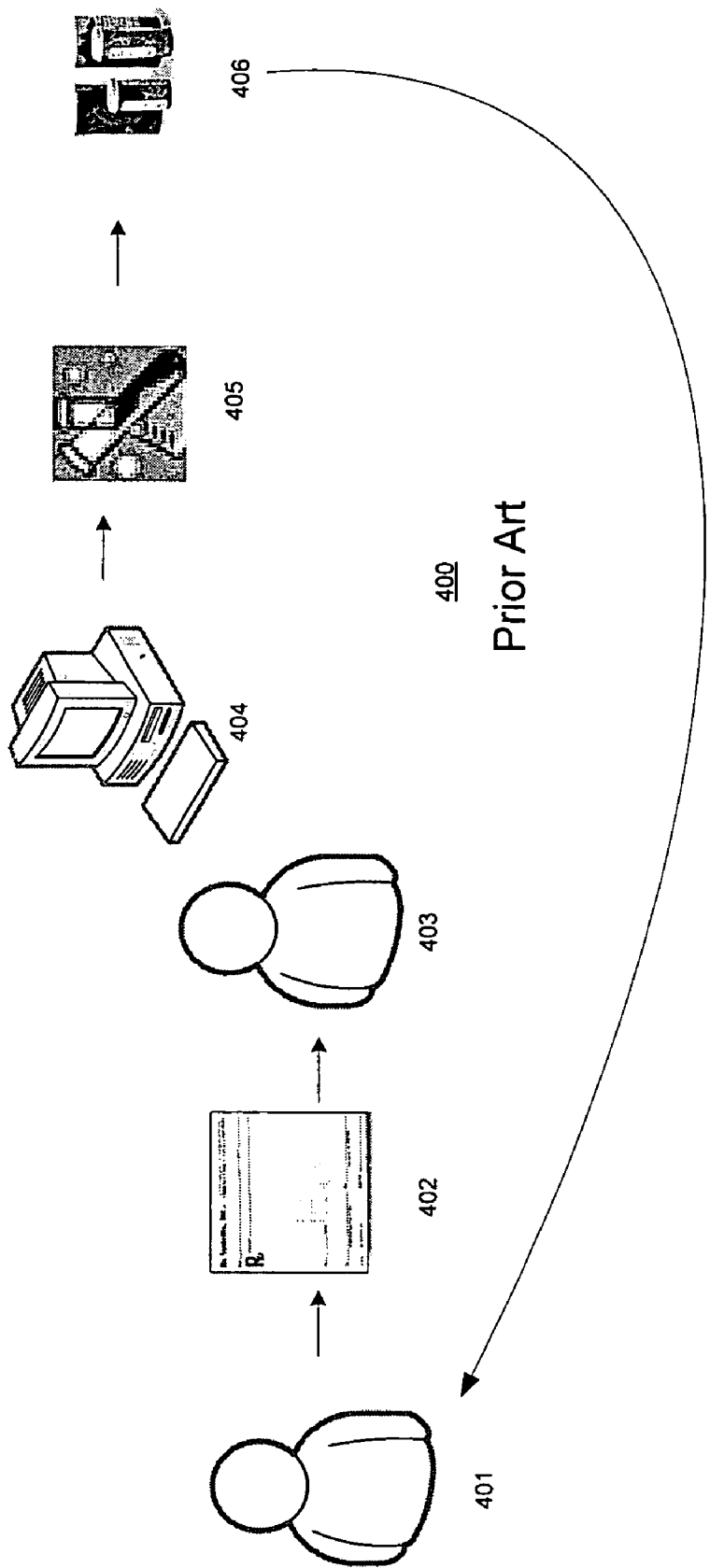
FIG. 4 illustrates a traditional pharmacy workflow.

FIG. 4 illustrates a workflow for a traditional pharmacy store 400. Even though this pharmacy store may be part of a large network of affiliated stores, the pharmacy store processes each locally received prescription work order in-house independent of any other store. A customer 401 drops off a prescription order 402 to a pharmacist, technician or clerk 403, who begins processing the prescription by entering information into a computer 404. Order entry may be the most time consuming portion of the process as each paper prescription is manually entered into the system by a pharmacy employee 403 who reads the prescription 402 and contemporaneously performs all the information processing steps (e.g., authentication, validation, inventory check, etc.) and physically prepares 405 and delivers the drug product 406.

In a pharmacy company comprising a network of affiliated stores, each pharmacy may be outfitted with identical equipment and inventory for processing a majority of standard drug orders. However, there are non-standard, or non-traditional drugs that require additional equipment, special materials, and sometimes additional technical expertise to process. Outfitting each store with similar equipment and inventory to account for specialty drugs could be prohibitively expensive. Providing expert personnel at each store location in a network may also be difficult, if not impossible. Also, more often than not, the demand for specialty drugs and even a portion of the traditional drugs, is not substantial enough to justify an additional expenditure in equipment, inventory, and human resources for each store.

If each store in a network of affiliated stores were identical (e.g., having the same equipment, personnel, and workload), existing information processing systems may be adequate to process the work orders because existing information systems are generally designed to capture and store the manually entered prescription orders for accounting and reporting purposes. Moreover, there would be little that could be done to improve system wide efficiency as each store is identical and processing would not need to be divided based on differences in store capacity. However, as mentioned above, equipping every single retail store or facility with the same resources for handling every drug prescription is prohibitively expensive. A more efficient strategy may be to break the prescription order processing workflow into portions that are more efficiently managed by different organizational units. Thus, a distributed processing scheme in which different organizational units, e.g., different retail stores, process different portions of a single work order may increase system efficiency.

Figure 5:
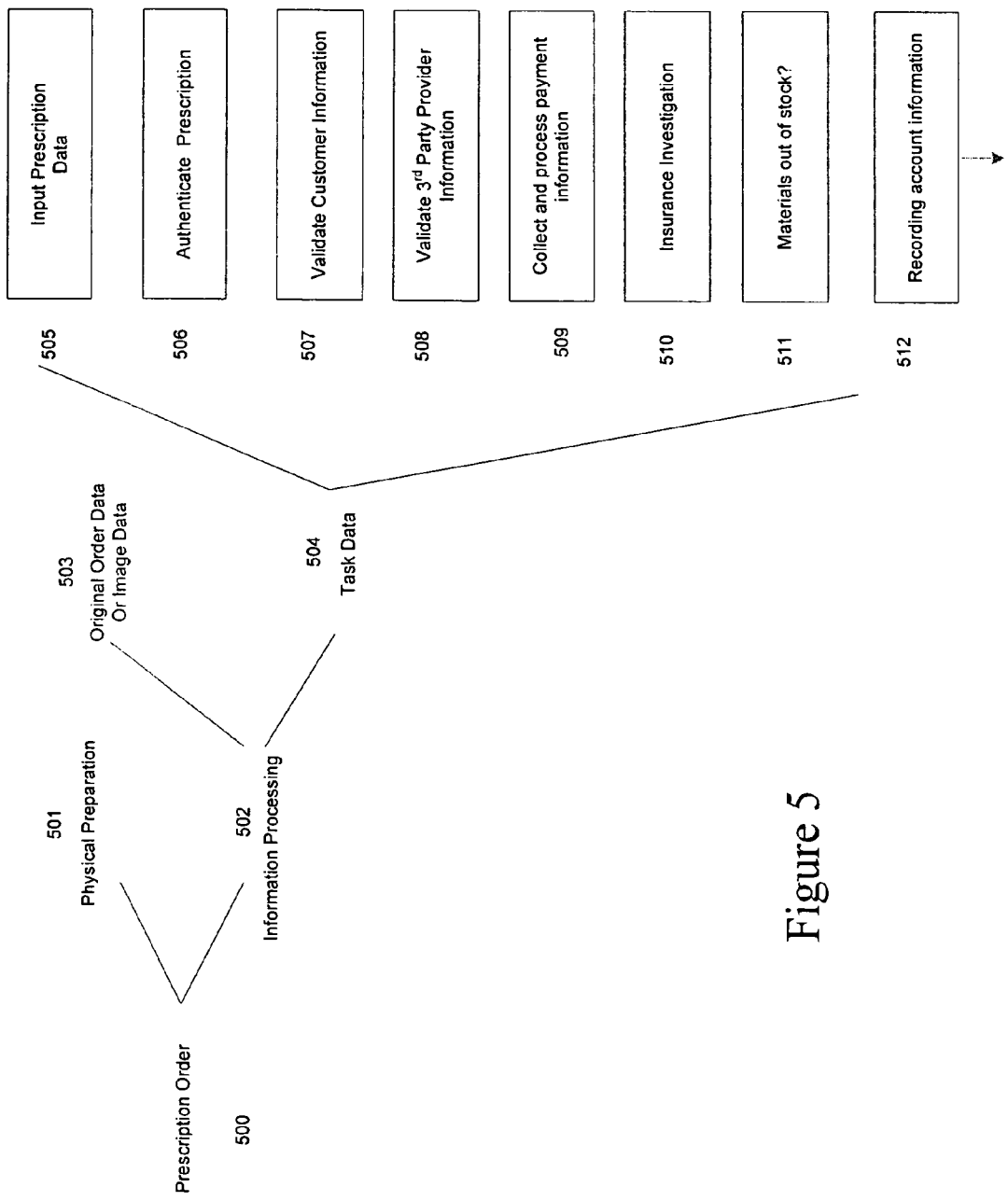
FIG. 5 illustrates a data composition diagram for pharmacy information processing.
Figure 6:
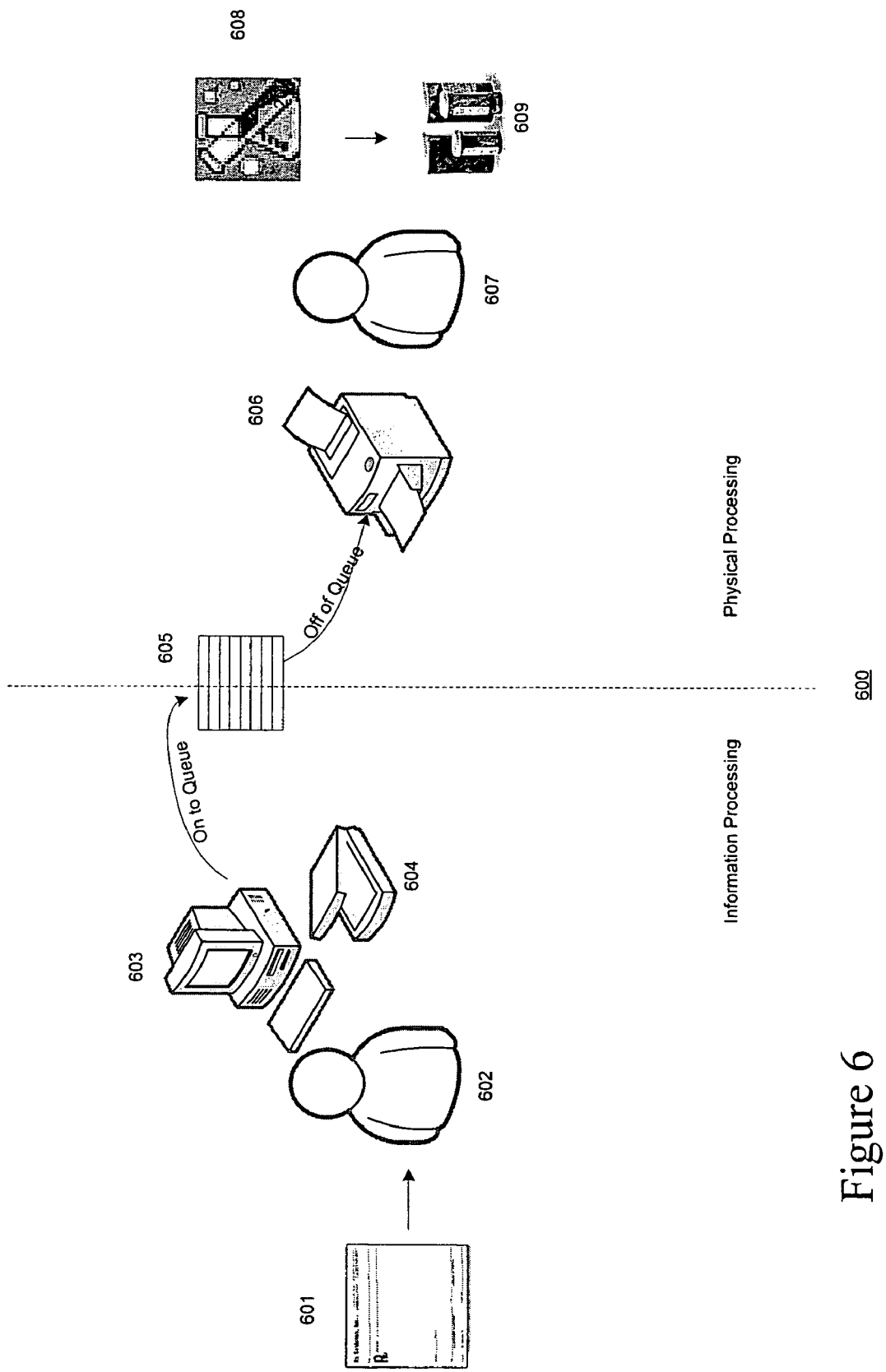
FIG. 6 illustrates a possible workflow division.

As illustrated in FIG. 5, processing of a pharmacy prescription drug order 500 may be separated into information processing of the order 501 and physical processing of the order 502. This is further illustrated in FIG. 6, where information processing 601-605 may be separated from physical preparation, which may include printing a label 606 based on instructions from a queue of entered work orders 605, and having a pharmacist 607 mix compounds 608 or retrieve a drug to fill a prescription drug order 609.

Information processing may include entering the original prescription order data into a system as well as all the steps that need to be performed to the order data before physically preparing the drug product. Because information processing of the order need not be performed at a particular location, the information processing portion of the order fulfillment process may be distributed to other organizational units for execution. This redistribution of work may be especially useful in a corporate owned or franchise retail store network where a corporate entity may have the power to enforce a retail store to process work from other affiliated stores and/or provide incentives for performing the work.

To enable geographic separation of workflow in which different entities and geographically separated personnel work on portions of a single prescription order, the pharmacy information system and method divides work into discrete units that can be distributed. The difficulty in dividing work in retail businesses that transact in paper work orders is that these work orders sometimes carry inextricable evidentiary relationships to a set of order processing steps. In a pharmacy business, for example, processing of a physical prescription may require constant reference to the original prescription document for verification and analysis, where the prescription document represents original order data and authorization to distribute a drug. In other words, order entry, which forms a significant portion of the information processing, may be broken into discrete steps, but because each step requires reference to original order data, order entry has not been easily separated in prior systems that generally require order entry and information processing to be entirely performed in one step and at one location.

Figure 7:
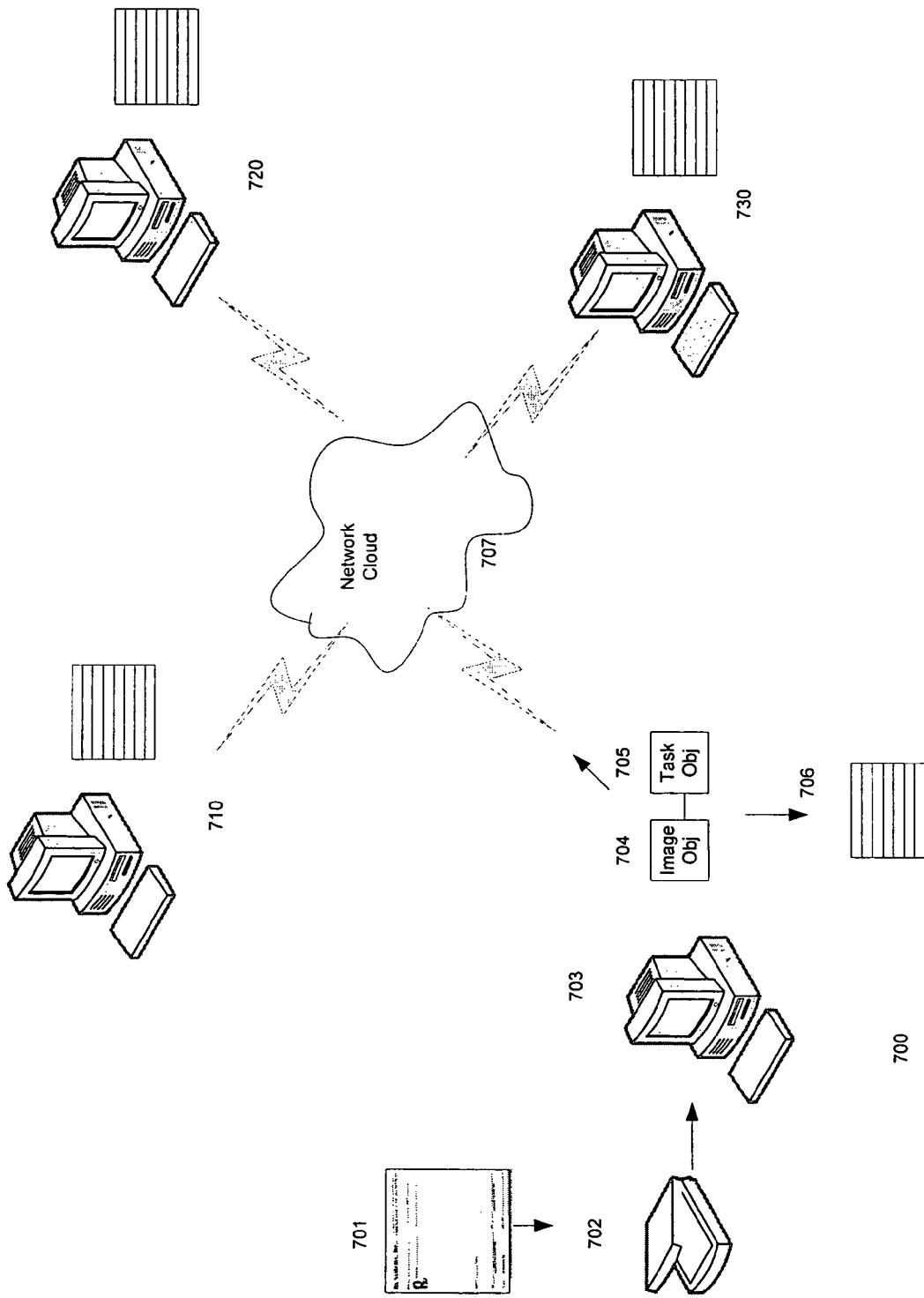
FIG. 7 illustrates a system for routing information processing work between pharmacy resources.

FIG. 7 illustrates a distribution system and method that may divide the information processing workload for a prescription order process. As discussed above, in order to divide the overall prescription information process into distributable portions, an ability to reference the original order data is provided. FIG. 7 illustrates that a physical paper work order, such as a prescription drug order 701, may be scanned into a network computer 703 at a particular retail store 700, thereby forming an electronic image object 704 of the drug order 701. This image object represents original order data that may be required for performing other steps of the work order process. In this embodiment of the claims an original order data (OOD) object may be formed using an image object. In other embodiments, additional documents such as certificate of medical necessity (CMN) forms, insurance cards, and laboratory results may also be scanned and captured by the OOD object.

FIG. 5 illustrates that information processing of the order can be decomposed into original order data 503, such as an image of the prescription order, and processing task data 504. The task data may be divided into portions of work performed to the original order data 503 to complete information processing 502. Thus, a task object may be associated with a set of discrete tasks, e.g., tasks 505-512. These tasks may be encapsulated into a single program entity called a task object 705 (See FIG. 7). The task object is used to carry and save the work performed on the prescription order, as represented by the OOD object, for each step of the order process. The task object may be passed from one organizational unit queue 706 to another 710-730 based on criteria such as a customer preference, product type, general pharmacy workflow, etc. By capturing the OOD into an object, the object may be used to provide information to process a task at each step of a workflow, without having to ground the entire process in one location. In this manner, workflow may be divided and distributed in a number of ways with little or no alteration of the information system. The information system may adapt to changing workflows and multiple workflows simply by routing the task object and/or OOD object to any queue within a network system, where the queue may represent a processing step.

In one embodiment, the OOD object may be stored in a central network server. A network computer (e.g., a client computer) may communicate with the central network server and may access an OOD object using a reference, which may be stored in the task object. The task object may be communicated between network computers to form a divided workflow, where each computer that receives the task object performs a portion of prescription order work that is captured by the task object. Alternatively, the task object may reside in a central network server and a reference to the task object may instead be communicated to a computer to indicate that that computer is tasked to perform a portion of work. (A reference to the OOD object may accompany the reference to the task object.) For example, an e-mail message from computer A to computer B may indicate that computer B is tasked to perform a portion of work on a prescription order, where the email contains a reference to the task object that will capture the work to be performed by computer B. In this case, computer B's email queue may act as a task queue.

In another embodiment, an image object is stored in a central repository managed by a pharmacy network server and a reference to the image object or a copy of the image object is routed to a network client computer to indicate that the computer is tasked to perform a portion of work using the image reference or image object copy. In this embodiment, the task object may be passed along with the image object reference or image object copy. Alternatively, the task object may be stored with the image object in the central repository and only a reference to the task object is routed with the image object reference or image object copy. For client computers that use a dial-up connection to a pharmacy network, instead of routing a task object, information entered using a copy of the image object may be uploaded to the server computer that stores a task object which is modified by the uploaded data. In one embodiment, uploading may be done by having a pharmacist call a touch-tone service to insert data into a network database.

Referring to FIG. 5, task data 504 may involve work related to inputting prescription data 505, authenticating a prescription 506, validating customer information 507, validating third-party provider information 508, collecting payment information 509, investigating insurance 510, determining out-of-stock status of materials 511, and entering accounting information into an accounting database 512. As the work is performed, the task object may store the processed information. The task object may consist of a table in a database which stores the process information. Alternatively, the task object may be a set of memory objects in a temporary computer memory that hold the work information temporarily until the task information is no longer needed, in which case the object is deleted, or until the task information is stored in a permanent medium.

Figure 8:
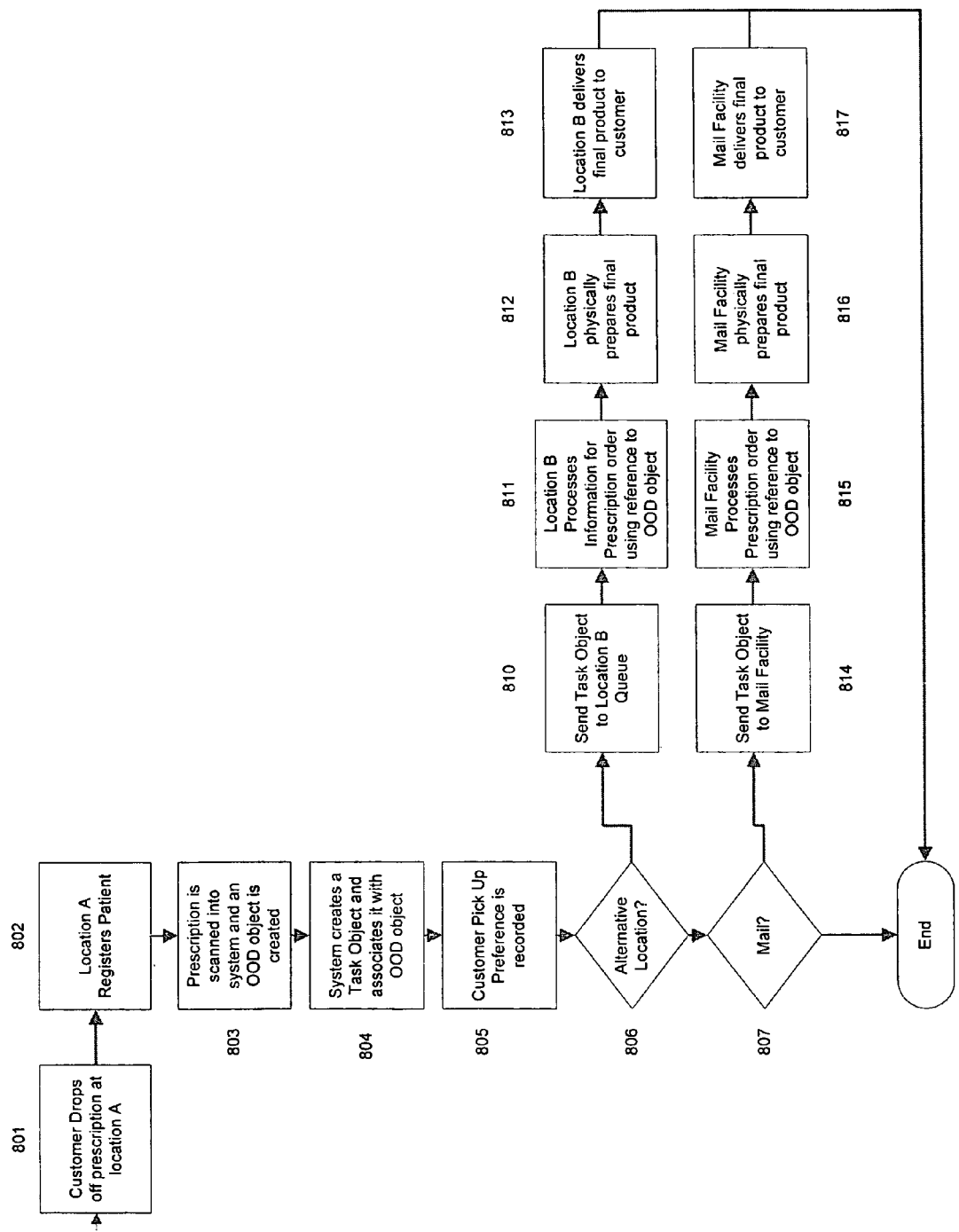
FIG. 8 illustrates a possible routing process for remote data entry and filling of a prescription order.

A prescription order workflow may be based on a number of factors. One such factor is customer preference. In certain situations, it may be useful to provide a customer the ability to drop off a prescription at a first location and pick up the filled prescription at a second location. FIG. 8 illustrates a possible routing process embodiment for this situation. A customer drops off a paper prescription at a location A 801. A pharmacy employee at location A registers the customer 802 by inputting new, or retrieving existing, account information, such as customer name, customer address, etc. The prescription is then scanned into the system and the system creates an OOD object 803. In this embodiment, the OOD object contains an image of the prescription. Next, the system creates a task object and associates the task object with the image object 804. The task object may contain the registration information. It should be noted that in a further embodiment, the registration information may form an account data object and the account data object may be associated with the OOD object as well as the image object. The customer's preference for an alternative pickup location is checked 805, 806 and the task object is routed to a pharmacy at location B 810. The task object may be sent with the OOD object with a reference to the OOD. Location B receives the task object in its work queue 810 and begins information processing the prescription order by referencing the OOD object 811. After the information processing is performed, physical preparation of the drug may be performed 812 and a final product may be delivered to the customer at location B 813. Alternatively, some pharmacy companies offer the option to mail a drug to a customer. In this case, a customer's preference for mailing may be determined 807, and the task object and OOD object or reference may be sent to a mail processing facility (MPF) 814. The MPF 814 performs similar processing to the alternate location processing described above, e.g., information processing 815, and physical preparation 816, except the delivery is performed by mailing the final product 817 to the customer.

Figure 9:
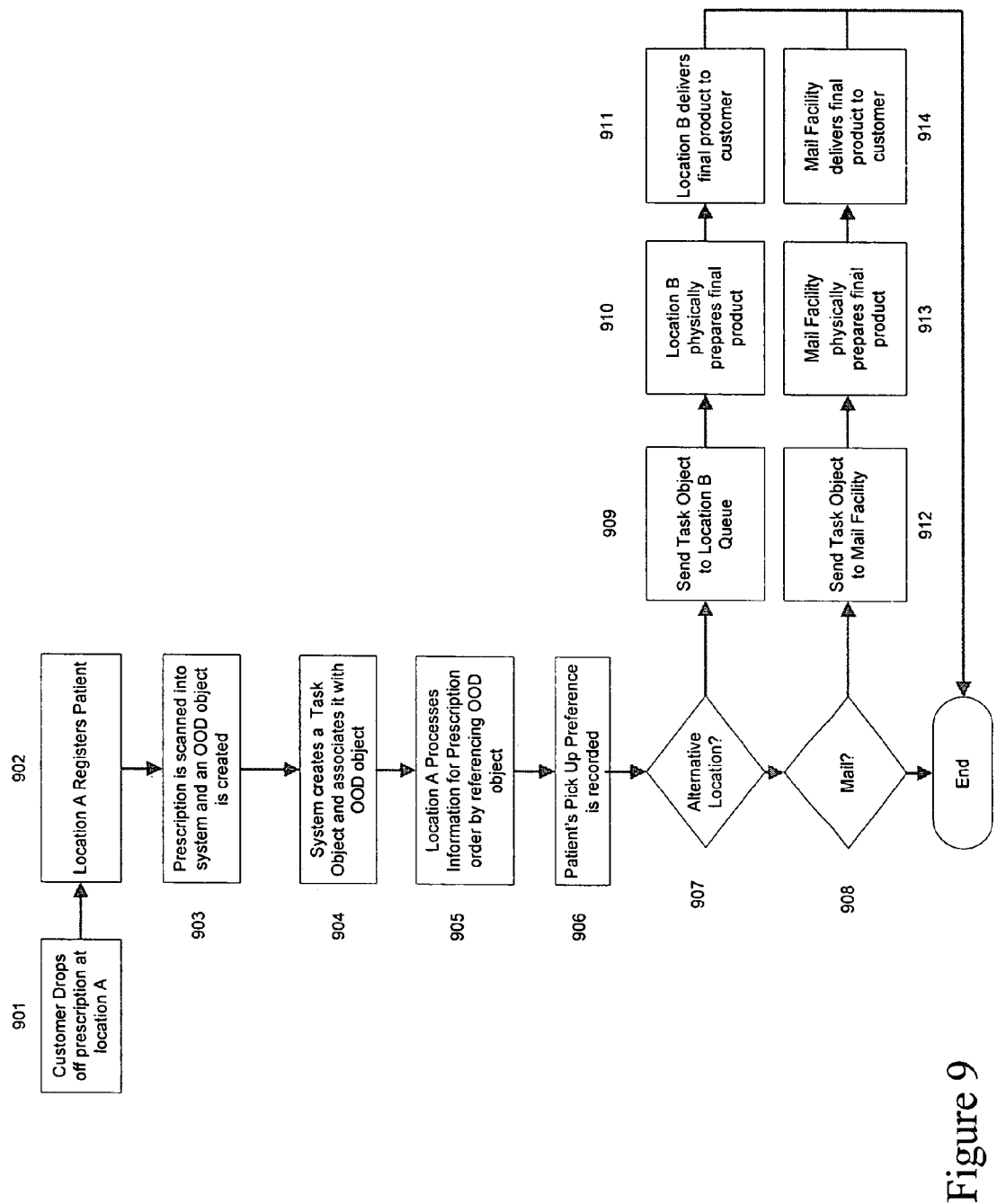
FIG. 9 illustrates a workflow for routing pre-processed work to a second pharmacy location for physical processing.

Another factor in determining workflow is pharmacy resource workload. A first pharmacy store may be less busy than a second pharmacy store, and thus the first pharmacy store may be underutilized while the second pharmacy store may be over utilized. In this situation, redistributing workload from the second pharmacy store to the first pharmacy store may improve overall network efficiency. This is illustrated in FIG. 9. After the customer drops off the prescription 901, pharmacy A registers the customer 902, the prescription is scanned to form an OOD object 903, a task object is created and associated with the OOD object 904, and information processing is completed at store A 905. Based on a customer's pickup preference 906, 907 the task object, which stores all the work performed on the OOD object, is simply sent to location B 909 where a label, or instruction set, may be printed for directing the physical preparation of the drug 910 and delivery to the customer 911. Alternatively, the completed task object could be sent to a mail order facility 908, 912 in which physical preparation may be performed 913 and the final product mailed to a customer 914. In an alternative embodiment, regardless of customer preference, a task object may be routed based on the capacity of the originating store and a second store and/or based on a level of completion of the task object (e.g., if processing of a task object is close to completion, the task object may be routed to a pharmacy resource to finish processing even if that resource is otherwise too busy to process less complete orders).

In an alternative embodiment, a prescription may be dropped off at store A, which simply scans the prescription order to form an OOD object and task object and routes the objects, or object references, to store B (similar to the workflow of FIG. 8), which has capacity to information process the order. After information processing the order, the task object may be routed back to store A for label/instruction printing, physical preparation of the drug, and delivery to the customer. This workflow may be applicable when store A has the equipment to physically prepare a prescription and store B does not. Alternatively, this workflow may be used when store A is too busy to perform the information processing portion of the order at the time the prescription is dropped off.

Figure 10:
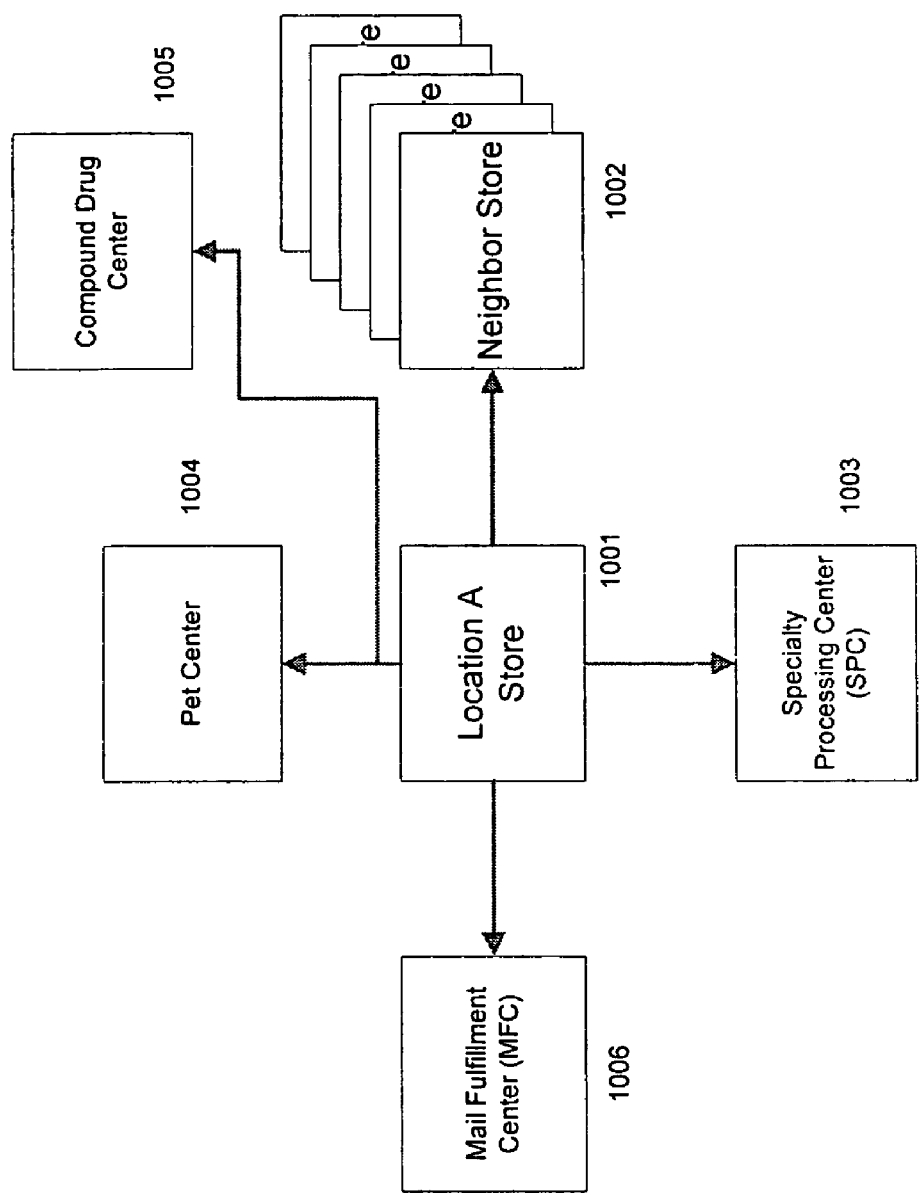
FIG. 10 illustrates a possible resource distribution of a pharmacy network.

FIG. 10 illustrates a resource distribution embodiment in which business functions are separated into specialized resource units. In this distribution schema, a retail store A 1001 may be connected to a network having neighbor stores 1002. The network may also have specialized facilities such as a specialized processing center ("SPC") 1003 which may be a separate facility that houses a set of experts who process a portion of the work for a prescription order. This set of experts may be used to provide the service needed for aggregated types of work orders. For example, as discussed above, certain work orders may require special treatment. These work orders may be aggregated and routed to an SPC which handles all such work orders, thereby consolidating resources to improve efficiency. Additionally, there may be facilities that contain equipment for specific, less common medications such as pet medicine or compound drugs. These resources may also be housed in separate facilities, e.g., a pet center 1004 or a compound drug center 1005. Consolidation of certain common functions such as fulfillment and mailing may also increase the speed at which prescriptions are processed. Thus, a mail fulfillment facility ("MFC") 1006 having both equipment and personnel focused solely on fulfillment and mailing may also increase network efficiency.

Because information processing may be divided and routed using the claimed method and system, a pharmacy network may dynamically assign process functionality to different facilities. For example, FIG. 10 illustrates a separate facility for pet, specialty, and compound drugs which may have the service expertise and/or equipment to process the specific drug prescriptions they are designated for. However, these facilities may not necessarily be limited by the availability of resources to have cross-functionality, e.g., an SPC store may have the capability to double as a retail store. Thus, the functionality of a particular facility may be dynamically assigned based on such things as network demand and efficiency. For example, while the equipment to process compound drugs is not provided at each facility, a subset of retail stores may hold these equipment resources and be capable of processing compound drugs. Thus, when demand for compound drugs is not high, only a few of the facilities having compound making equipment may be designated as compound centers and process compound prescription orders (meanwhile the facilities may continue to operate as retail stores, or other specialty facilities). When demand increases, more stores having the compound equipment may be made available and designated as compound facilities to process the extra demand, even while the same facility continues to function in other roles.

Dynamic assignment of functionality may also apply to service expertise. For example, while the embodiment of FIG. 10 discloses a single specialty processing center for housing specialty drug experts, drug experts may be located at other facilities, including retail stores and other specialty stores. The pharmacy network system may include a table or data object containing the location and distribution information of service personnel and resources. Whenever additional resources are needed to handle increased demand or other workload events, the distribution table may be accessed to determine which additional resources may be activated.

In another embodiment, service personnel may not necessarily need to be located at a particular facility or retail store in order to perform work processing. For example, a pharmacy company may implement home location workers. In this case, home location workers may be assigned login parameters that authorize the workers to participate in a portion of the information processing. The login parameters may determine whether a worker may process, for example, a portion of a specialty drug order. The login parameters may be assigned only to workers having a level of expertise to process the portion of the workflow they are authorized for. It should be noted that even at an SPC, workers may be required to login with authorization (e.g., credentials indicating a threshold pharmacy expertise level) to process specialty drugs. Alternatively, a facility may be designated with a certain expertise level (e.g., the SPC) such that any user on a network computer at the facility is authorized (using another means) to process the specialty prescriptions. Moreover, specialty prescription orders may be routed to pharmacy resources based on a pharmacy expertise level of the pharmacy resource.

As discussed above, a customer's preference may be a determining factor for routing an order to an alternative location for pick-up. Other situations may arise, however, which may also determine routing of the work order and/or limit customer pick-up options. For example, an out-of-stock situation may occur in which an alternative location may need to be designated from a list of stores having the materials.

During information processing of a prescription, a computer associated with a prescription drop-off store may determine an inventory capacity of a selected pharmacy resource to process the prescription order. For example, the computer may check its own inventory database to determine if its pharmacy has the material to fill the order. Alternatively, a customer may initially select an alternate pharmacy store for order pickup. If the selected resource or location has insufficient inventory capacity, the customer may pick up the prescription at another alternate store or may wait until inventory is available at the originally selected resource. The customer may also choose to have the prescription mailed to a designated location from a mail center. In this case, the computer may determine the inventory capacity of the selected alternate store. If there is sufficient inventory capacity, then the prescription may be routed to the selected pharmacy resource location. However, a selected prescription pickup resource, including the prescription drop-off store, may have insufficient inventory capacity to fill the prescription order. This may occur in prescriptions for traditional drugs, pet medication, and specialty drugs. An insufficient inventory capacity may indicate that the materials necessary to prepare the prescription is insufficient or unavailable, e.g., out of stock. When a first choice location is determined to have insufficient inventory capacity, the system may perform an inventory check of other pharmacy resource locations and determine a set of alternate stores or mail centers having sufficient inventory capacity to fill the order. This may be performed, for example, by using a database table or data object, or communicating with another computer associated with a pharmacy resource. In one embodiment, the list of alternate stores are stores in close proximity to the originating store. These alternate stores may be called neighbor stores 1002, as illustrated in FIG. 10. In another embodiment, the list of alternate stores are stores with a lower workload. In another embodiment, the list of alternate stores are stores in close proximity to the originating store with a lower workload.

Figure 11:
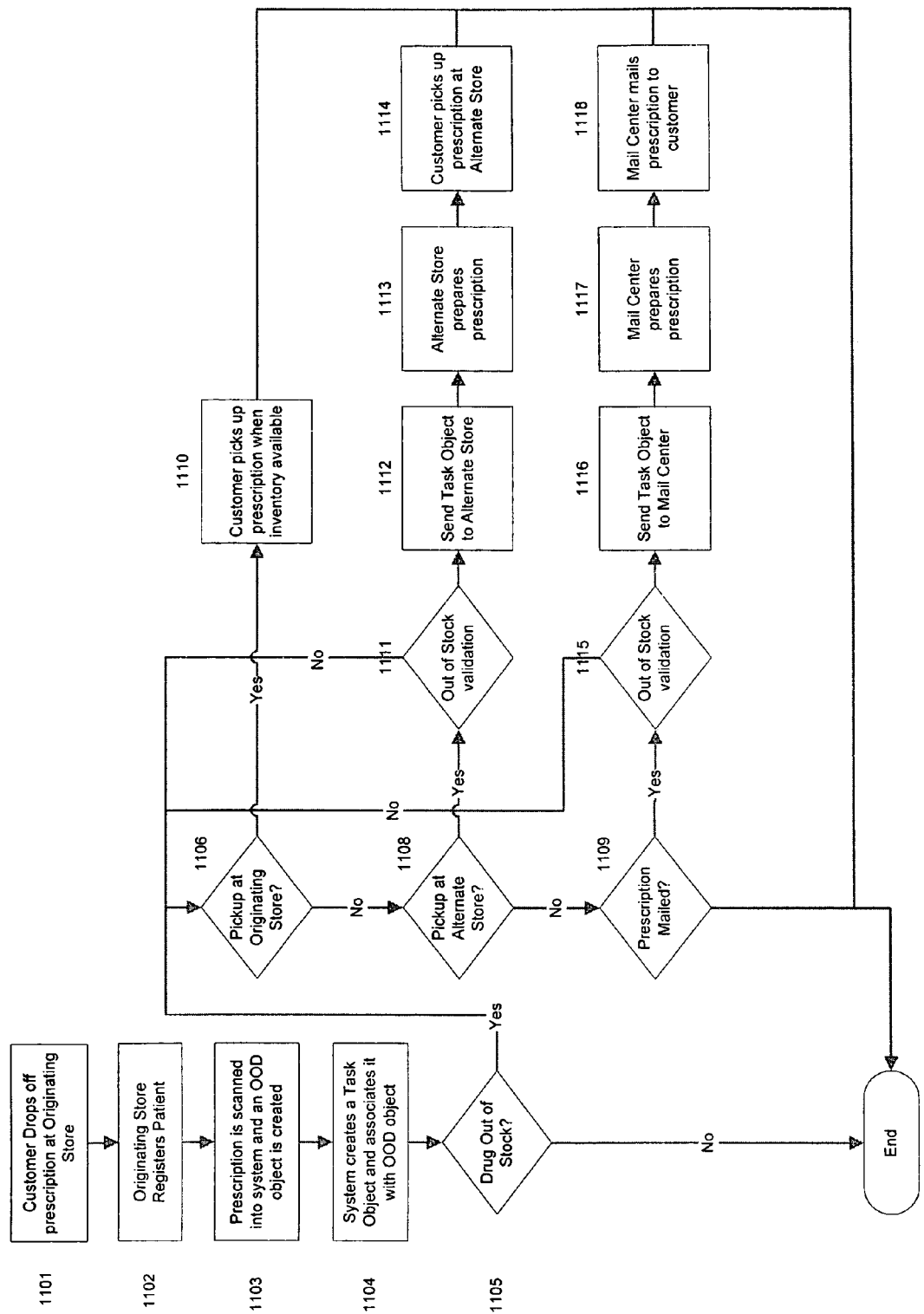
FIG. 11 illustrates a possible workflow of an out of stock situation.

FIG. 11 illustrates a possible workflow for an out of stock drug situation. A customer drops off a prescription at the originating store 1101 and is registered by a pharmacy employee 1102. The originating store scans the prescription into a system and creates an OOD object 1103, and associates a task object 1104 with the OOD object. If the system determines the drug is out of stock at the originating store 1105, the customer may decide to pick up the prescription at the originating store 1106 when inventory becomes available 1110, or may decide to pick up the prescription at an alternate store 1108 or have it mailed to them 1109. If the prescription is to be picked up at an alternate store 1108, an out of stock validation is performed for the alternate store 1111. If the drug is in stock at the alternate store, the task object is routed to the alternate store 1112, the prescription is filled 1113, and the customer may pick up the prescription at the alternate store 1114. If the prescription is to be mailed to the customer 1109, an out of stock validation is performed for the mail center 1115. If the drug is in stock at the mail center, the task object is routed there 1116, the prescription is filled 1117, and the prescription will be mailed to the customer 1118.

In an alternate embodiment, a first network computer associated with the location in which a prescription order is dropped-off may determine a first set of alternate pharmacy locations having inventory capacity to fill the prescription. The first network computer may also determine a subset of the first set of pharmacy locations which match additional criteria, such as proximity to the first location and workload. In one embodiment, the first network computer may only show the subset of pharmacy locations with minimal workload, unless a parameter is set to display the entire first set.

Another alternative store routing situation occurs when the prescription involves compound drugs or pet medications. Compound drugs are drugs that are comprised of more than one ingredient. While the information processing may be performed either at the originating location or at a specialty location, the physical preparation may have to be performed at the specialty location, such as a designated compound center or pet center having the necessary material and equipment to fill the prescription. Thus, a computer associated with a pharmacy resource may identify an equipment type associated with the prescription order in order to determine what kind of material, equipment and/or equipment configuration is necessary to process the order. The equipment type may be determined from prescription data contained in the task object. For example, the equipment type may be determined to be a compound drug prescription order when the prescription order requires two or more base ingredients to fill. The equipment type may also be determined by a designated parameter of the task object.

Specialized equipment necessary to fill a compound drug or pet medication prescription may not be in existence in every pharmacy facility. However, there may be a set of pharmacy facilities which contain the equipment but are not active specialty centers. Alternatively, the set of pharmacy facilities may have the equipment, but the equipment may not be configured appropriately. Thus, a pharmacy network computer may determine a set of pharmacy locations having equipment capacity based on the existence of equipment and whether that equipment is available for use. The equipment capacity determination will depend on the equipment type associated with the prescription order. The equipment capacity may involve accessing a pharmacy database containing a table of pharmacy resources and associated equipment and equipment configuration for those resources. For example, a network computer may access the table and find stores that have equipment matching the equipment type of a prescription order.

After determining that a pharmacy resource has the equipment capacity to process a particular drug, that pharmacy resource may be designated as a center, e.g., a compound center or pet center, and the pharmacy workflow may route the task object to the compound center or pet center for physical preparation and/or information processing of the order. In one embodiment, the customer may pick up the prescription at any location, including the originating store, an alternate store, the compound center, or have it mailed from the compound center. In a mail process embodiment, the task object and/or image object associated with the prescription order may be placed in a mail queue for preparation of the prescription at a compound center and shipping via courier or mail to a desired pickup location. In another embodiment, the customer may only receive the filled prescription at the compound center or have it mailed from the compound center.

Figure 12:
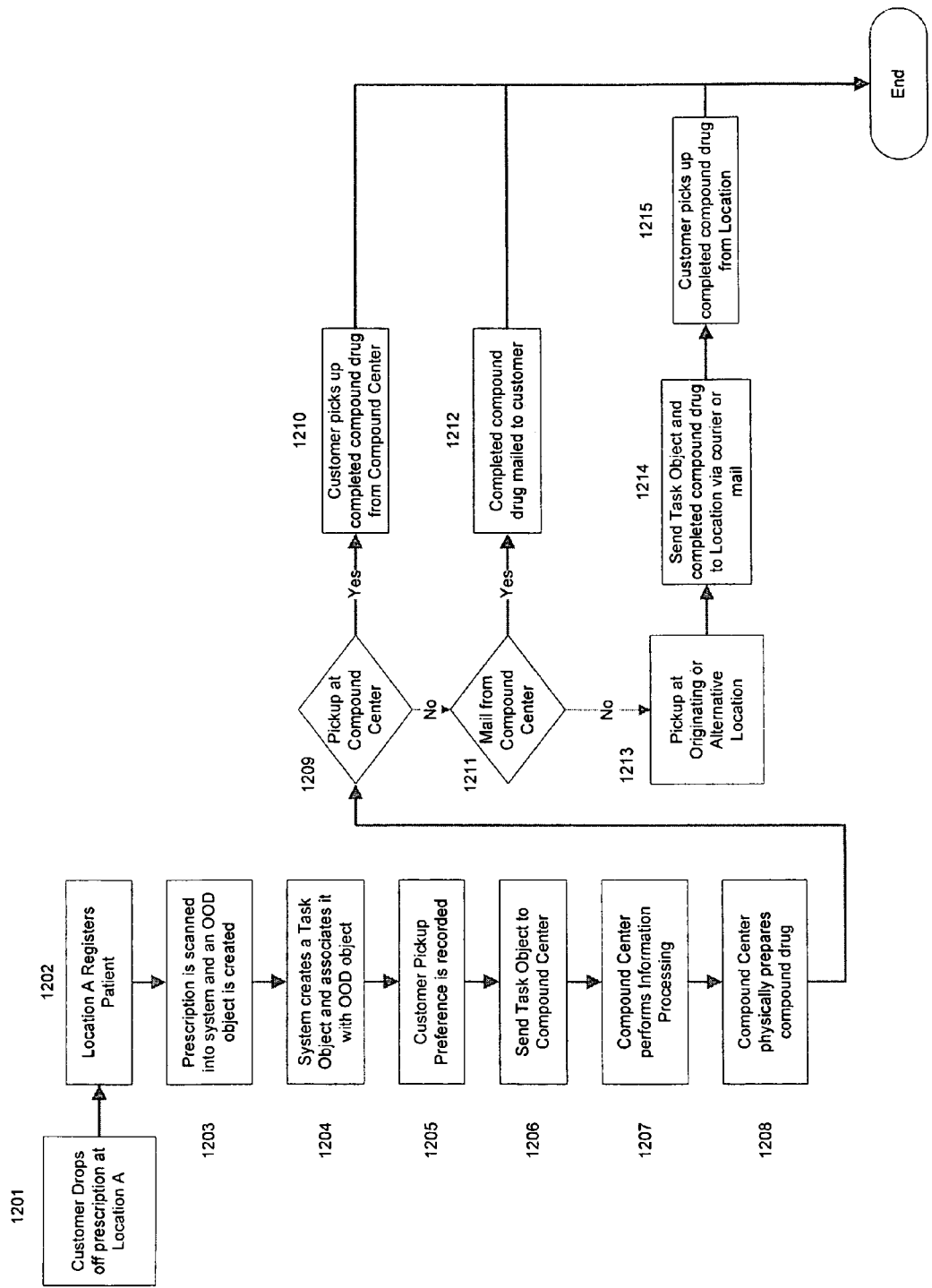
FIG. 12 illustrates a workflow for a compound prescription order.

FIG. 12 illustrates a possible workflow for a compound drug prescription process. A customer drops off a prescription at Location A 1201 and is registered by a pharmacy employee 1202. Location A scans the prescription into a system and creates an OOD object 1203, associates a task object 1204 with the OOD object, and records the customer's pickup preference 1205. The task object and associated OOD object are routed to a compound center 1206 for information processing 1207 and physical preparation 1208. After completion of physical preparation 1208, the compound drug can be picked up by the customer from the compound center 1209, 1210 or mailed from the compound center to the customer 1211, 1212. The compound drug may also be picked up from the originating store or an alternate store 1213, in which case the task object and compound drug are routed to the desired pickup location 1214 for pickup by the customer 1215.

In an alternate embodiment, a first network computer associated with the location in which a prescription order for a compound drug or a pet medication is dropped-off may determine a first set of alternate pharmacy locations having the equipment capacity or drug product to fill the prescription. The first network computer may also determine a subset of the first set of pharmacy locations which match additional criteria, such as proximity to the first location and workload. In one embodiment, the first network computer may only show the subset of pharmacy locations with minimal workload, unless a parameter is set to display the entire first set.

Another factor in determining workflow is specialized workers. Specialized workers may be needed for certain types of prescriptions that require additional expertise to fill. A specialized processing center ("SPC") (as illustrated in FIG. 10) may be used to process a subset of prescriptions that require expert servicing. In this case, a pharmacy workflow may entail routing the task object to an SPC in which experts may perform the specialized work. Thus, the information processing may not be completed at any one location or organization unit, but is divided among at least two organizational units which may be geographically separated. In one embodiment, the SPC is tasked to provide only expert servicing, where fulfillment is performed at a separate fulfillment resource. In another embodiment, the SPC may be partially integrated with the fulfillment function for specific drugs that require additional verification or specific administration, e.g., some drugs may require expert review prior to dispense via mail or a retail store.

Specialty drugs may be highly expensive designer drugs that require enhanced customer service. For example, for high priced designer drugs, payment processing may be complicated. Some third party insurance plans may not cover these drugs, or alternatively, they may require additional steps to process (other than those steps required to process traditional drugs). For example, additional verification may be needed, verification that a normal retail store pharmacist may not be trained to handle or capable of handling. This may be required for drugs at risk for fraudulent procurement. Alternatively, depending on the policy of the customer's insurance company, some designer drugs may require non-traditional pharmacy billing procedures before these drugs can be dispensed.

Specialty drugs may also include rare disease drugs that require additional expertise and a risk management process (e.g., for dispensing and/or distribution) that general retail store pharmacists may not be trained to provide. Specialty drugs may include drugs that need additional resources to administer (e.g., syringes and/or other supplies). A specialist may need to evaluate clinical data, to collect additional clinical data (which may involve further communication with a customer or prescriber), to make adjustments to a prescription, or to perform supplemental research in order to fill the order.

A computer associated with a pharmacy resource may identify a specialty drug type associated with the prescription order in order to determine what kind of expertise or additional processing is necessary to process the order and whether the prescription order needs to be routed to an SPC. The specialty drug type may be determined from prescription data contained in the task object. For example, the specialty drug type may be determined to be a specialty drug prescription order when the prescription order requires clinical data, additional supplies, expert review of prescription data, and/or an insurance investigation. The specialty drug type may also be determined by a designated parameter of the task object.

Figure 13:
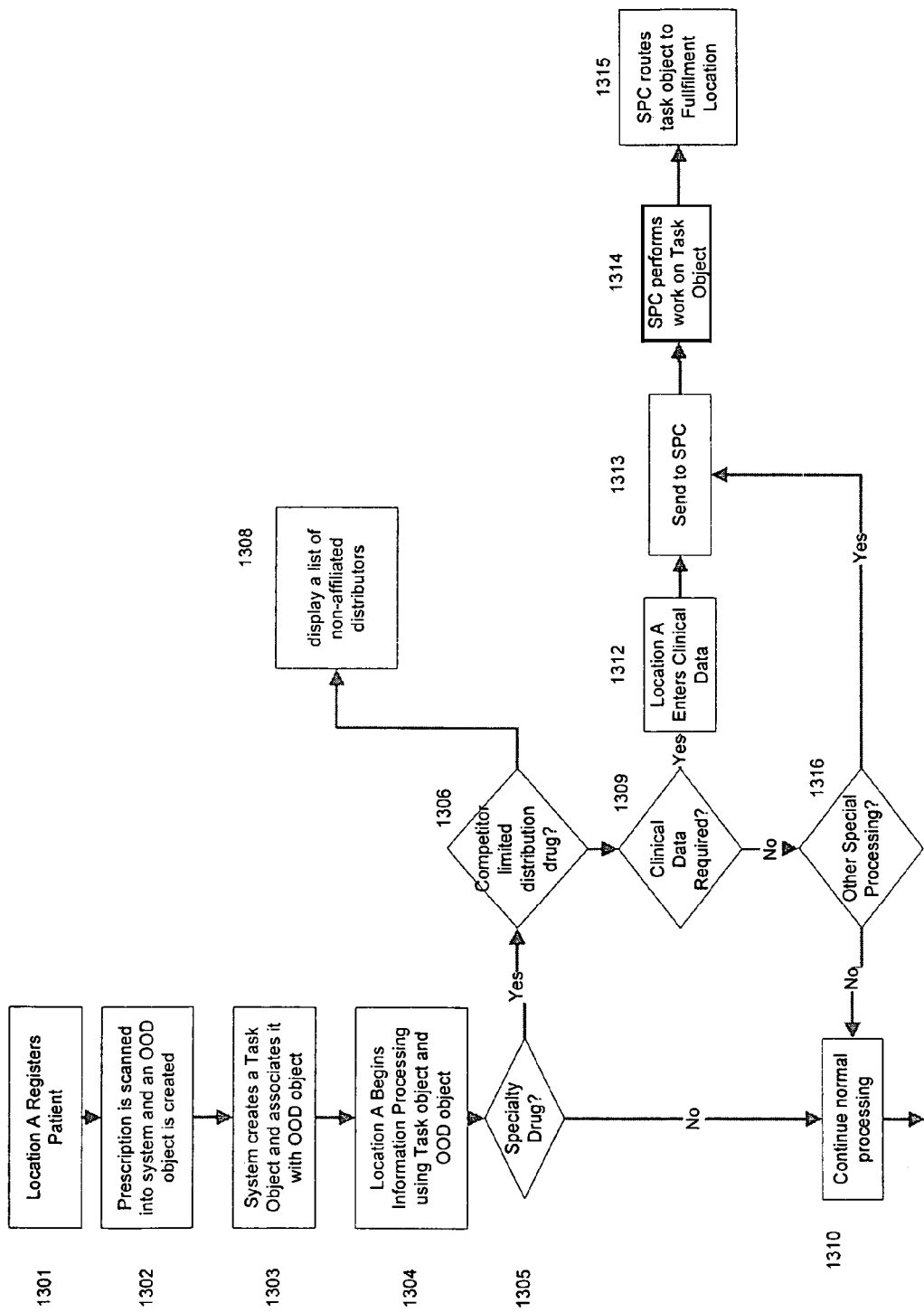
FIG. 13 illustrates a possible specialty drug workflow.

FIG. 13 illustrates a possible workflow for a specialty prescription process. Location A receives a prescription and registers the patient 1301, and scans the prescription into a system 1302. An OOD object 1302 and task object 1303 are created and associated with one another. Location A then begins information processing the order 1304. If the drug is a specialty drug 1305, the system then determines if the drug is a competitor limited distribution drug 1306 or an inter-pharmacy limited distribution drug. If the drug is a competitor limited distribution drug, then the system may display a list of non-affiliated distributors 1308 for the drug. If the drug is not a competitor limited distribution drug, then it may be an inter-pharmacy limited distribution drug that requires clinical values 1309. Location A then begins entering clinical data based on the OOD object 1312. An image may be selected for association with the clinical values data for a specialty drug prescription. This image may be for example, a portion of the OOD object that contains information for the clinical data. The task object and associated OOD object or OOD object reference is then routed to a specialty processing center (SPC) 1313 where a set of experts may evaluate the clinical data 1314. Other specialty drug processes may require immediate sending to an SPC 1316. Once the specialty processing is performed, the task object may be routed to a fulfillment center 1315. The fulfillment center may be the originating store, an alternate store, a specialized fulfillment center, or a mail processing facility, depending on the type of drug and a customer preference.

A software embodiment may use a clinical value screen for displaying and capturing clinical values using an image of prescription or clinical data. Clinical values may be divided into hard and soft edits. Soft edits may be annotations associated with the image for the clinical data. The soft edits may be values that are not immediately critical to the drug's administration and may not be checked for missing or out of range values, but may be read and checked by a specialist at a later stage.

The clinical values crucial for filling a specialty drug are marked as hard edits. The hard edits may undergo an initial verification process to check whether the values are missing or out of range based on given defaults and/or based on the specific specialty drug. For out of range values, the clinical value may be flagged for additional checking by a specialist. Once the initial clinical values are recorded, the script is sent to a specialized processing center (SPC) where an expert pharmacist familiar with the drug can evaluate and review the clinical data 1314 and assess the propriety of the prescription and/or further steps to take in processing the prescription. At block 1314, an SPC expert may call the customer for further information in order to verify the clinical data or to ensure that the drug is appropriate for the customer. Additionally, the specialty drug may require that the expert pharmacist coach the customer on how to administer the drug. This may be the case, for example, when a supply kit is necessary, or when the drug requires a syringe or other resource (e.g., a nurse, physician, or other third party) to administer.

Block 1316 checks to determine if there is other processing steps necessary to fill a specialty drug prescription other than checking clinical values. Thus, the SPC at blocks 1313-1315 may perform additional processing other than clinical value processing. For example, the SPC may perform an additional insurance investigation to determine if a third party plan covers a prescription for highly expensive designer drugs. Alternatively, the SPC may be responsible for enforcing a background check of a patient/customer for certain drugs that have a high risk of fraudulent procurement.

In one embodiment of specialty drug processing, a credit or payment investigation may require that a portion of the information stored in the task object be sent to a third party for verification. This may occur, for example, by having a pharmacy network computer extract the relevant data portion of the task data and communicate this data to a third party server. This data portion may be associated with payment information. The third party server may be associated with an insurance company or a creditor. The pharmacy network computer may send the data portion and request a payment and/or a payment verification.

Figure 14:
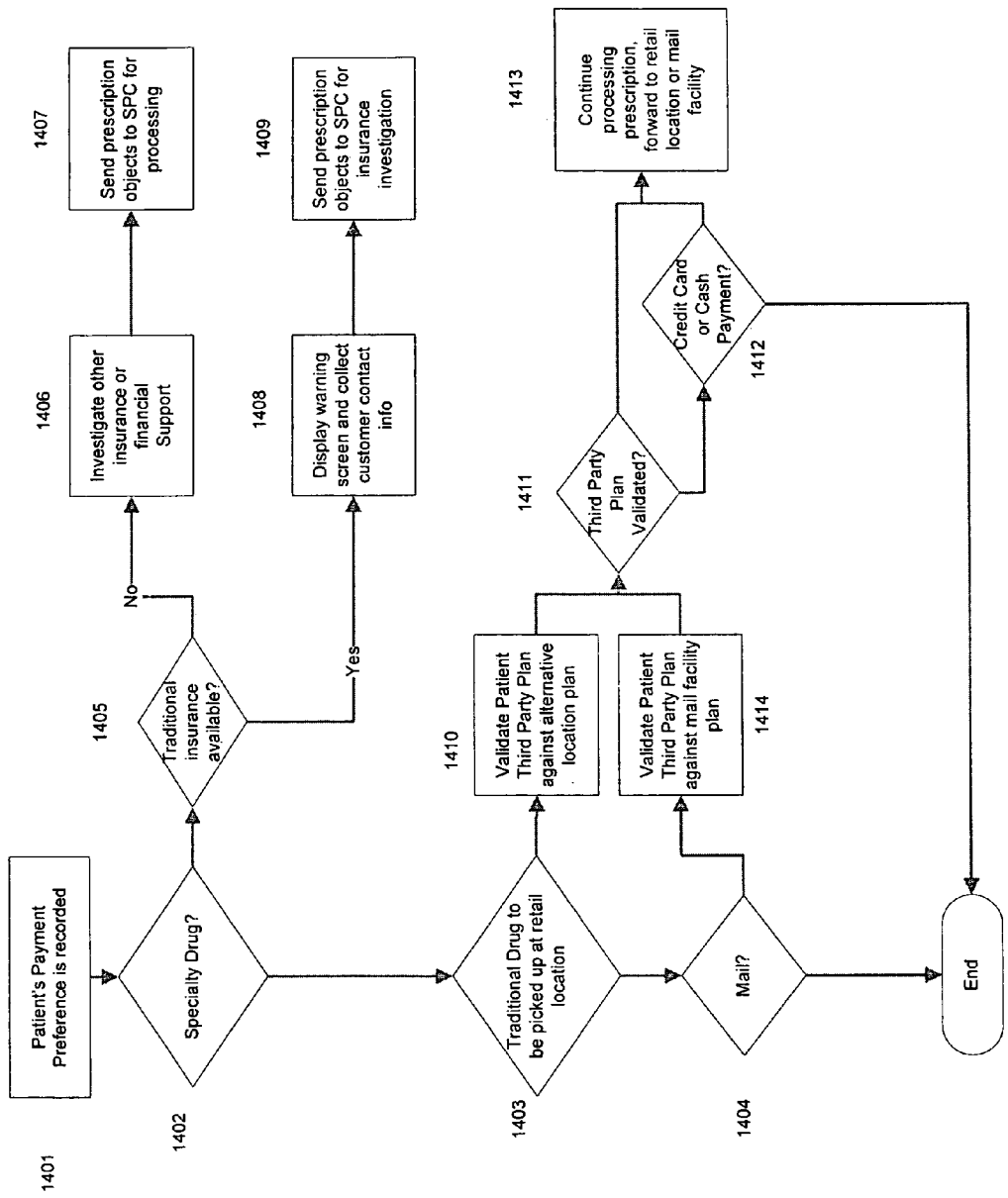
FIG. 14 illustrates a possible payment workflow.

FIG. 14 illustrates a payment system embodiment. A customer dropping off a prescription at a first location A may select a payment method 1401 as part of an initial prescription order placement. Prepayment options may include a third party insurance plan, cash, a check or a check equivalent, or a credit/debit card. Alternatively, in some instances, the customer may decide to make a payment where the prescription is fulfilled. A check to determine if the prescription involves a specialty drug is made at block 1402. If so, then block 1405 determines if traditional insurance may be available for the drug. If traditional insurance may be available, an indicator may caution that insurance may be available based on general insurance parameters but that additional information must be collected and verified 1408. The information collected is then sent to an SPC for processing 1409. In some cases, traditional prescription insurance may not cover specialty drug products or a customer may simply be uninsured. The retail pharmacy may offer an option to investigate alternative financial options such as non-traditional prescription insurance 1406. In instances where non-traditional insurance may be an option, an embodiment may simply collect customer contact information and pass the order to an SPC to finish processing, e.g., by performing an insurance investigation or other third party payer investigation 1407. For traditional prescriptions that will be delivered to a customer at a retail location 1403, a third party plan is validated 1410 based on data associated with another retail store's plans. If the third party plan is validated 1411, the prescription continues its regular processing 1413. If validation fails, then alternative retail location options may be processed 1412. If validation is successful, prescription processing continues 1413. If the prescription is to be mailed 1404, the same process applies, except that the third party validation may occur against a mail facilities third party plan 1414.

In a routed prescription process, a customer delivers a prescription order at a location A and then accepts delivery at a second location B. A confirmation document is preferably printed using a computer at location A and handed to the customer after the receipt and initial processing of the prescription order at location A. The order confirmation document may be printed at Location A with Location B information. The confirmation document may provide proof of payment if prepayment was made at Location A. Otherwise, the confirmation document may simply identify the prescription order using, for example, a prescription identifier. The prescription identifier may be a bar code printed on the prescription order such that a pharmacist at a pickup location may simply scan the confirmation document (e.g., using a computer at location B) to retrieve prescription status information, e.g., retrieve the task object and/or image object.

In one embodiment, customers may take their order confirmation document to any non-fulfillment store to pre-pay their prescriptions. The order confirmation document may include identifying reference information, such as a prescription identifier, that may be used at a particular pharmacy resource to access a task object and/or image object for a prescription associated with the document, where the task object may contain payment information. The prescription identifier may correspond to an identifier parameter contained in the task object. This identifier parameter may be used for authentication purposes. Alternatively, the task object may be associated with an customer object that contains this information. Scanning the bar code may initiate a request by a computer at a pharmacy location to have the account object routed to that location. The account object may be in a first queue associated with a network computer of a first pharmacy (e.g., a prescription drop-off location or a preferred pick-up location) and routed to a queue of a second computer at a different pharmacy for payment or prepayment (e.g., before a prescription is ready for pickup). A pharmacy employee may scan the bar code on the order confirmation document to determine if the customer has paid any amount for the prescription and deduct that from the total sale price of the prescription order. The customer may then pay in full or partially pay the remaining balance. The task object or associated customer object may be updated accordingly with the payment status. This may involve adjusting a customer debit account associated with the task object for the prescription.

Customers may take their order confirmation document to a fulfillment location to inquire on the status of their prescription. The pharmacy employee at the fulfillment store may scan the barcode on the order confirmation document to retrieve the information. The system may return the status of the prescription, including the payment status. Should the status of the prescription be paid in full (which may be indicated by displaying a dispensing permission indicator at a network computer), then the prescription may be delivered to the customer. If there is a balance, the customer will be required to pay the balance first, before the prescription is dispensed. If there is an overpayment (e.g., for an adjustment from a third party plan payment), the customer may be refunded the overpayment at delivery time. The order confirmation documents may not only serve as proof of payment, the document may also be used to authenticate the customer for specialty drugs.

In the case of a refund, the bar code of an order confirmation document will be scanned by a pharmacy employee. If prescription has a SOLD status, a refund without prescription is blocked. In this case, a prescription label may be needed in addition to the confirmation document for a refund, in order to ensure that a physical prescription is returned to a facility. Refunds for a prescription routed to another store before SOLD status may occur at any time. Refunds for a prescription routed to MAIL may only be done through a special mail return process. This special mail return process may involve returning the drug to an MFC or using a return envelope or box. Refunds for a script routed to another store after SOLD status may only occur at a fulfillment store that is designated to accept returns. Retail stores may all be designated as return capable or only a subset of retail stores may be designated as return capable based on efficiency and customer policy.

In one embodiment, the customer may be limited to prepaying only the full amount of the prescription, where partial prepayment is not allowed. In another embodiment, prepayment may only occur at a non-fulfilling location. Shipping charges may be recorded separately from the prescription price and tax. This may allow the shipping prices to be handled separately for a later negotiated refund. Price information may include prescription price, tax, and shipping charges. Taxes may be based on local tax of the fulfillment store. Pre-payment may be made at any organizational unit in the network in which the task object may be routed for processing, thus enabling customers the option to pay for their prescriptions at any location. In another embodiment, Internet payment may be also be an option. In this embodiment, an Internet application may be designed to interface with an account system for a pharmacy company. Alternatively, a customer may have created an express pay account, where a customer has registered an account in which funds may be automatically deducted whenever a prescription has been entered. In this case, prepayment is automatic.

Figure 15:
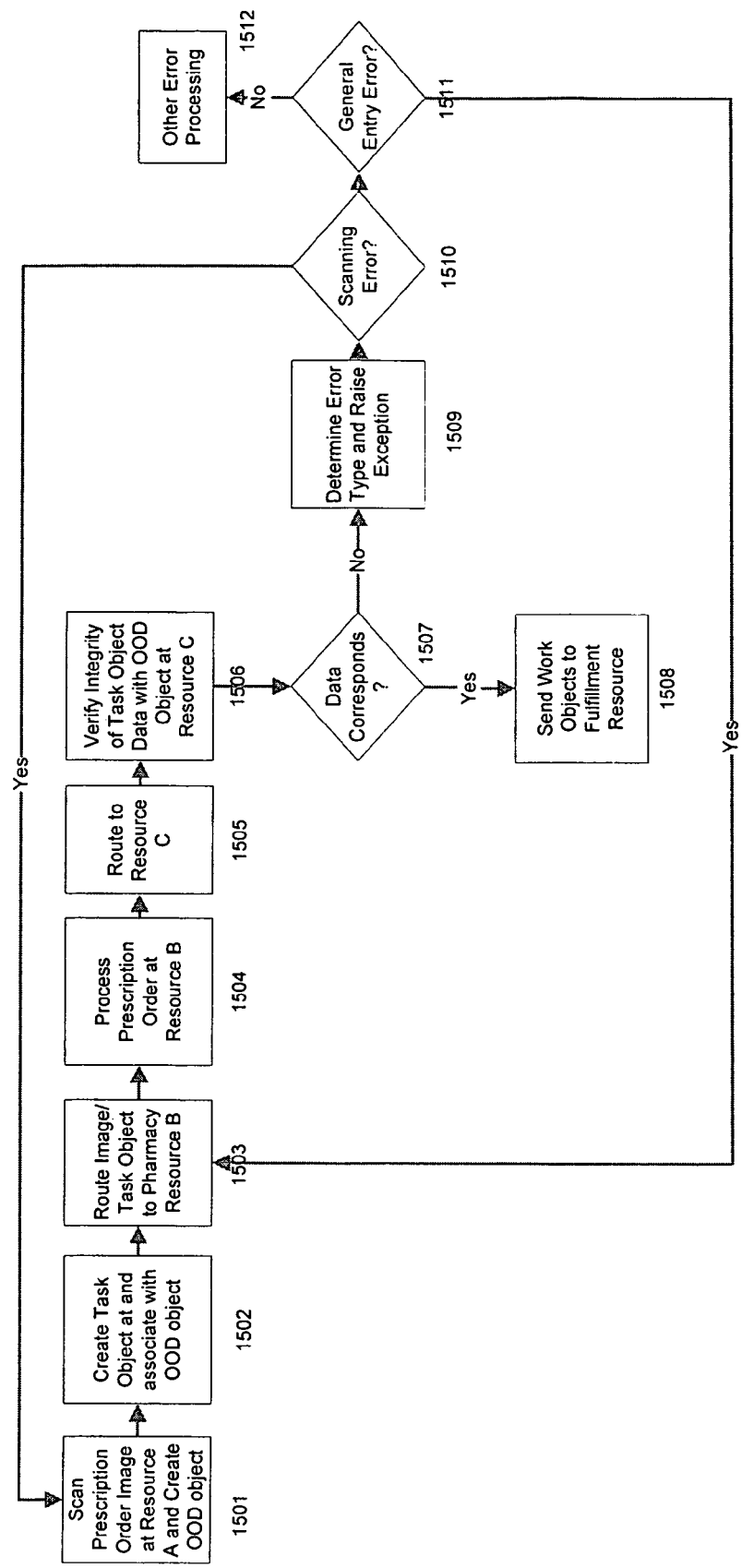
FIG. 15 illustrates a possible order verification workflow.

While quality of product is important in most businesses, quality of product is especially important in the pharmacy business where drug safety is critical. Because accuracy of prescription data is critical in producing a safe drug, in addition to entering data based on original prescription data, information processing requires verification of entered data. FIG. 15 illustrates a possible verification process. An image may be scanned in at a first pharmacy resource A and captured by an OOD object 1501, which is then associated with a task object 1502. The prescription order objects (e.g., OOD/image object and task object) may be sent to a second pharmacy resource 1503 for a portion of order processing 1504 before being sent to a third pharmacy resource C 1505 for verification processing 1506. Verification may be performed by specialized pharmacists that primarily focus on verification processing. Verification may entail examining a prescription image and reviewing entered data to ensure that the information in image form corresponds to data stored in an associated task object. If the data matches 1507, then the prescription order objects may be routed to a pharmacy resource for fulfillment 1508. If the data does not correspond, then the pharmacy resource may determine the type of error and raise an exception 1509. Pharmacy resource C may then route the prescription order to another pharmacy resource based on the error type. For example, if a scanning error occurred 1510, the prescription order objects may be routed back to the originating pharmacy resource A. If a general data entry exception occurs 1511, the prescription order objects may be routed back to a pharmacy resource (e.g., pharmacy resource B) for correction. Other error types may also be processed 1512.

A data exception parameter may be used to indicate whether an inconsistency is detected during the verification process and the nature of the inconsistency. Various errors may cause an inconsistency between original order data captured in the image object and the data contained in a task object. A scanning error is one type of error. A scanning error may indicate that a scanned image in the image object may have poor quality and is unreadable. An entry error is another type of error. An entry error may be caused by a pharmacist entering information at any stage of the process. When a data entry error is detected, the source of the error may be determined, for example, by using a log of users involved in each step of the work process. Data entry errors may themselves be tallied and recorded as well. The routing of the prescription order objects may be based on the exception parameter. For example, when the exception parameter indicates a scanning error in which the image object is unreadable, the image object and/or task object may be routed back to a location or a pharmacy resource that first originated the order or that first scanned the image. In another example, when the data entry error indicates a data entry error for a portion of work, the prescription order objects may be routed back to a pharmacy resource that performed the portion of work and/or that is responsible for the portion of work.

In one verification embodiment, a log of data entry errors by a pharmacy resource may be used to calculate an accuracy measure for that pharmacy resource. The pharmacy resource accuracy measure may be used to determine a pharmacy resource efficiency. Routing may be further based on the accuracy and/or efficiency of the pharmacy resource. For example, high risk drugs that may require less tolerance for error may be routed to higher accuracy pharmacy resources.

In another verification embodiment, certain automated checking of entered data may occur during a stage of the information processing. For example, automatic spell checking may be used. In this case, a data exception may cause an alarm to be generated at a network computer to indicate a potential error. In yet another embodiment, text recognition software may be used to enter portions of the prescription. In this case, an image of a prescription order may be scanned in and inputted to the text recognition software. The software may output a text file of entered data corresponding to the scanned prescription image. The verification process may then begin on the outputted electronic text. The electronic text may be placed in a task object before the verification process or the electronic text may be verified first before creating a task object to capture the verified text.

To further ensure integrity of information processing, a document management system may be applied to the routing and work processing. The image object may have a lock parameter which is used to selectively allow access to the image and/or selectively prevent routing of the image when the parameter is set to lock. The image object may be prevented from being routed, referenced, copied, or otherwise accessed by a second network computer when a first network computer is already performing a portion of work using the image object. In an embodiment where the task object is routed, the task object may also contain a lock parameter that is used to prevent access to the task object in a similar manner to the image object. The lock parameter may also be used to prevent access to the task object or image object based on the identity of a user. This may be the case when a pharmacist does not have the requisite access level to process a portion of work for the prescription order.

As discussed above, the claimed system divides a work process into discrete units that can be distributed to different entities. Distributing workload may increase the efficiency of a network by routing work from overutilized stores to underutilized stores. Efficiency may also be increased by aggregating low volume specialized drug processing into one center and routing work to this center. Specialty centers may contain specialized equipment, expert workers, or both. Facilities may be designated as specialized centers based on certain network events such as demand spikes. Facilities may also perform multiple functions.

What is claimed is:

1. A method of managing payment information as part of prescription fulfillment on a network pharmacy system comprising a plurality of facilities including a first and second pharmacy location connected by an information processing system, the first and second pharmacy locations at separate geographic locations with each of the first and second locations having at least one employee and each of the plurality of facilities having a facility computer server, the method comprising:

receiving a prescription drug order for a customer at the facility computer server of the first pharmacy location participating in the network of pharmacy resources;

receiving from the customer a preferred pick up location for the customer's prescription drug associated with the prescription drug order, wherein the preferred pick up location is the second pharmacy;

storing an original order data (OOD) object, at the information processing system, containing a set of information received from a customer during placement of the prescription drug order;

creating a task object file that is associated with the OOD object and unique to the OOD object, the task object file storing a discrete set of tasks to be performed for filling the prescription order and that is used to carry and save work to be performed and work completed on the prescription order;

collecting payment information;

storing a data portion associated with payment information in the task object file;

determining if a payment investigation is required for the payment information;

when the payment investigation is required: extracting a relevant part of the data portion from the task object and communicating the relevant part of the data portion to a third party;

modifying the task object file via the facility computer server to change the work tasks associated with the OOD object based on at least one of payment information contained in the OOD object and a set of customer parameters including the customer's preferred pick up location;

based on the customer's preferred pick up location, routing the task object file from a first queue stored on first facility computer server at the first pharmacy location to a second queue stored on the second facility computer server at the second pharmacy location over the information processing system connecting the first and second pharmacy locations, wherein routing the task object includes one of communicating the task object file or communicating a reference to the task object file; and dispensing the prescription drug associated with the OOD object to the customer at the second pharmacy location.

2. The method of claim 1, wherein the OOD object comprises at least one of an image of a medical card, check, money order, and credit cart, and wherein modifying the task object file comprises populating the task object file with information associated with the image.

3. The method of claim 1, wherein modifying the task object file comprises populating the task object file with at least one of customer billing information, payment option information, and payment status information.

4. The method of claim 1, wherein modifying the task object file comprises storing a customer payment option, and wherein the payment option comprises at least one of cash, wire transfer, credit card, check and third party insurance.

5. The method of claim 4, wherein the payment option is restricted based on the type of drug associated with the prescription order.

6. The method of claim 4, wherein the payment option is restricted based on the cost of the prescription order.

7. The method of claim 1, further comprising querying an object containing third party insurance information based on the task object file to determine an insurance payment portion associated with a prescription, and wherein modifying the task object file comprises storing the insurance payment portion information in the task object file.

8. The method of claim 7, wherein the insurance payment portion is deducted from a customer debit account referenced by the task object file.

9. The method of claim 1, further comprising routing one of the task object file and OOD object from the first queue associated with the facility computer server of the first pharmacy location to a third queue associated with a network computer based on a payment option stored in the task object file.

10. The method of claim 9, wherein the network computer is associated with a third party creditor.

11. The method of claim 9, wherein the facility computer server of the first pharmacy location creates an order confirmation document when the task object file is to be routed to the second facility computer server at the second pharmacy location, based on the customer selection of pick up location.

12. The method of claim 11, wherein the order confirmation document contains a prescription identifier.

13. The method of claim 11, wherein the prescription identifier is represented by a bar code on a physical confirmation document, and further wherein the bar code is scanned at the second facility computer server at the second pharmacy location to access at least one of the task object file and OOD object associated with the prescription order.

14. The method of claim 11, further comprising displaying a dispensing permission indicator at the second pharmacy location when a prescription identifier of the confirmation document matches a prescription identifier associated with the task object file.

15. A pharmacy workflow payment system implemented by a computer system, the system comprising:
- an image object, created when receiving a prescription order for a customer at the first pharmacy resource at a first location, the image object stored on the computer system, associated with the prescription order;
- a task object file associated with the prescription order, wherein the task object file is stored on the computer system, containing a set of discrete tasks representing work required to complete processing of the prescription order; and
- a workflow manager, stored on the computer system, that is configured to identify a customer requested pickup location of the task object and to route the task object file based on a customer requested pickup location to a second pharmacy resource at a second pharmacy at a second location geographically separate from the first location by one of communicating the task object file or communicating a reference to the task object file, wherein the workflow manager is associated with a first pharmacy resource at a first location.

16. The system of claim 15, wherein the workflow manager is configured to select a data portion of the task object based on the payment parameter and sends the portion to a server associated with a third party.

17. The system of claim 16, wherein the workflow manager is configured to request at least one of a payment and a verification of payment from the third party server.

18. The system of claim 15, wherein the workflow manager is configured to initiate a refund payment transaction when both an order confirmation document and a prescription label is scanned and authenticated by a network computer, wherein the prescription label is associated with a physical prescription container.

19. A non-transitory computer-readable medium having computer-executable instructions for routing a prescription order based on a payment parameter of a customer and a customer preference of a second pharmacy for picking up a drug associated with the prescription order, the non-transitory computer-readable medium comprising:
- a first program at a facility computer server of a first pharmacy that receives original order data and the customer preference of the second pharmacy for pick up and creates an original order data object;
- a second program at the facility computer server that creates a task object file that stores a discrete set of tasks to be performed for filling the prescription order and that is used to carry and save work to be performed and work completed on the prescription order and associates the task object file with the original order data object;
- a third program at the facility computer server that identifies a payment parameter associated with a prescription order; and
- a fourth program at the facility computer server that routes the task object file based on the payment parameter by one of communicating the task object file or communicating a reference to the task object file; and
- a fifth program at the facility computer that routes the original order data object and the task object file to the second pharmacy geographically separate from the first pharmacy.

* * * * *